(12) United States Patent
Ichinose et al.

(10) Patent No.: US 9,242,009 B2
(45) Date of Patent: Jan. 26, 2016

(54) COMPOSITIONS AND METHODS TO TREAT NEURODEGENERATIVE DISEASES

(71) Applicant: The General Hospital Corporation, Boston, MA (US)

(72) Inventors: Fumito Ichinose, Brookline, MA (US); Eizo Marutani, Boston, MA (US); Kotaro Kida, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/415,322

(22) PCT Filed: Jul. 17, 2013

(86) PCT No.: PCT/US2013/050905
§ 371 (c)(1),
(2) Date: Jan. 16, 2015

(87) PCT Pub. No.: WO2014/015047
PCT Pub. Date: Jan. 23, 2014

(65) Prior Publication Data
US 2015/0209438 A1    Jul. 30, 2015

Related U.S. Application Data

(60) Provisional application No. 61/672,533, filed on Jul. 17, 2012.

(51) Int. Cl.
| | |
|---|---|
| *A61K 31/381* | (2006.01) |
| *A61K 31/385* | (2006.01) |
| *A61K 31/4436* | (2006.01) |
| *A61K 31/166* | (2006.01) |
| *C07D 339/04* | (2006.01) |
| *C07D 339/06* | (2006.01) |
| *C07C 323/41* | (2006.01) |
| *C07C 327/48* | (2006.01) |
| *A61K 47/48* | (2006.01) |
| *C07D 409/12* | (2006.01) |
| *C07C 323/60* | (2006.01) |
| *A61K 45/06* | (2006.01) |
| *A61K 31/13* | (2006.01) |
| *A61K 31/16* | (2006.01) |
| *A61K 33/04* | (2006.01) |
| *C07D 409/14* | (2006.01) |

(52) U.S. Cl.
CPC ............... *A61K 47/481* (2013.01); *A61K 31/13* (2013.01); *A61K 31/16* (2013.01); *A61K 31/166* (2013.01); *A61K 31/381* (2013.01); *A61K 33/04* (2013.01); *A61K 45/06* (2013.01); *C07C 323/41* (2013.01); *C07C 323/60* (2013.01); *C07C 327/48* (2013.01); *C07D 339/04* (2013.01); *C07D 339/06* (2013.01); *C07D 409/12* (2013.01); *C07D 409/14* (2013.01); *C07C 2103/74* (2013.01)

(58) Field of Classification Search
CPC .. C07D 339/04; C07D 339/06; C07D 409/12; C07C 323/41; C07C 327/48; A61K 31/381; A61K 31/385; A61K 31/166; A61K 31/4436
USPC ................ 548/12; 560/147; 514/75, 432
See application file for complete search history.

(56) References Cited

U.S. PATENT DOCUMENTS

| | | |
|---|---|---|
| 5,061,703 A | 10/1991 | Bormann et al. |
| 8,039,009 B2 | 10/2011 | Rastogi et al. |
| 2006/0035888 A1 | 2/2006 | Jonas et al. |
| 2010/0048726 A1 | 2/2010 | McDonald et al. |
| 2010/0081723 A1 | 4/2010 | Jonas et al. |
| 2011/0046232 A1 | 2/2011 | Mahashabde et al. |
| 2011/0165252 A1 | 7/2011 | Dedhiya et al. |
| 2011/0236439 A1 | 9/2011 | Yang et al. |
| 2012/0004318 A1 | 1/2012 | Rastogi et al. |

FOREIGN PATENT DOCUMENTS

| | | |
|---|---|---|
| WO | 2006/037623 | 4/2006 |
| WO | 2008/009127 | 1/2008 |
| WO | 2009/109501 | 9/2009 |

OTHER PUBLICATIONS

International Search Report and Written Opinion mailed Dec. 19, 2013 in international application No. PCT/US2013/050905, 13 pgs.

International Preliminary Report on Patentability in International Application No. PCT/US2013/050905, issued Jan. 20, 2015, 14 pages.

Caliendo et al., "Synthesis and biological effects of hydrogen sulfide (H2S): development of H2S-releasing drugs as pharmaceuticals," J Med Chem., 53: 6275-6286 (Sep. 9, 2010).

Chen et al., "Gene profiling reveals hydrogen sulphide recruits death signaling via the N-methyl-D-aspartate receptor identifying commonalities with excitotoxicity," J Cell Physiol., 226:1308-1322 (May 2011).

Cheung et al., "Hydrogen sulfide induced neuronal death occurs via glutamate receptor and is associated with calpain activation and lysosomal rupture in mouse primary cortical neurons," Neuropharmacol., 53:505-514 (Sep. 2007).

DeLeon et al., "Passive loss of hydrogen sulfide in biological experiments," Anal Biochem., 421:203-207 (Feb. 1, 2012).

Lee et al., "Effects of hydrogen sulfide-releasing L-DOPA derivatives on glial activation: potential for treating Parkinson disease," J Biol Chem., 285:17318-17328 (Jun. 4, 2010).

(Continued)

*Primary Examiner* — Raymond Henley, III

(74) *Attorney, Agent, or Firm* — Fish & Richardson P.C.

(57) ABSTRACT

The specification provides compositions and methods to treat neurodegenerative diseases.

20 Claims, 19 Drawing Sheets

(56) References Cited

OTHER PUBLICATIONS

Olson, "The therapeutic potential of hydrogen sulfide: separating hype from hope," Am J Physiol Regul Integr Comp Physiol., 301:R297-R312 (Aug. 2011).

Predmore and Lefer, "Development of hydrogen sulfide-based therapeutics for cardiovascular disease," J Cardiovasc Transl Res., 3:487-498 (Oct. 2010).

Qu et al., "Hydrogen sulfide is a mediator of cerebral ischemic damage," Stroke, 37:889-893 (Mar. 2006).

Reiffenstein et al., "Toxicology of hydrogen sulfide," Annu Rev Pharmacol Toxicol., 32:109-134 (1992).

Protocol of OGD for SH-SY5Y cells

Protocol of OGD for primary cortical neurons

FIG. 6A
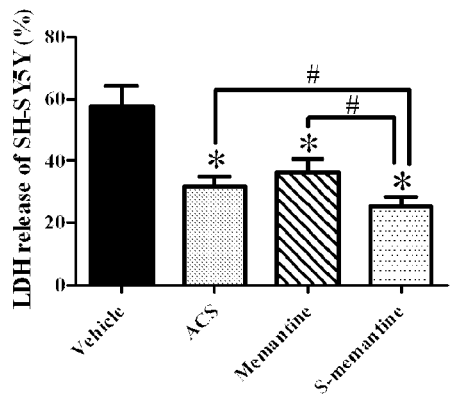
FIG. 6E
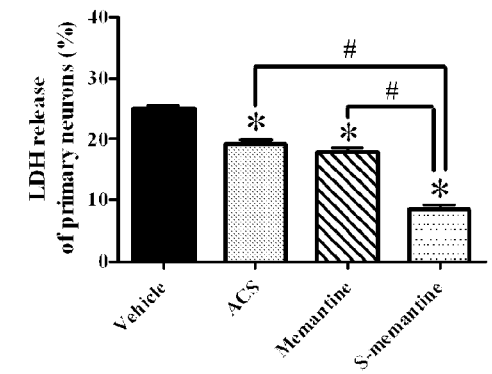
FIG. 6B
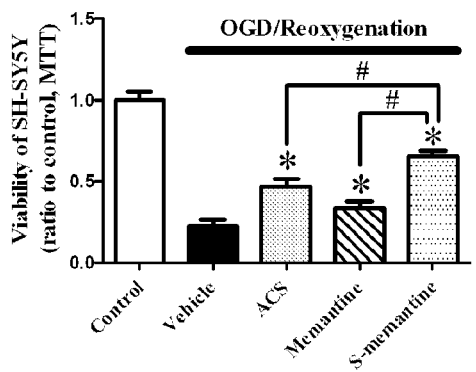
FIG. 6C
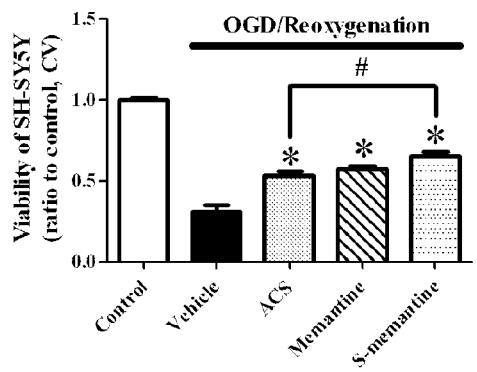
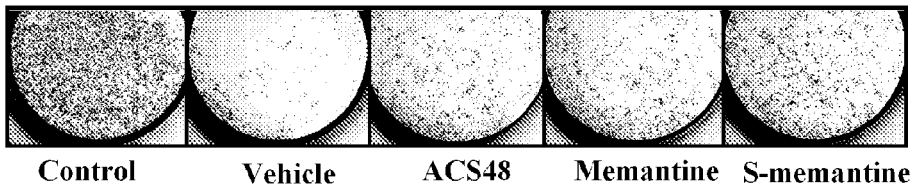
FIG. 6D FIG. 9A
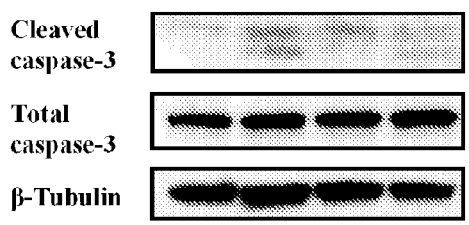
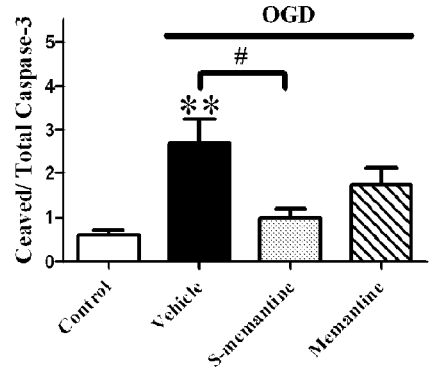
FIG. 9B
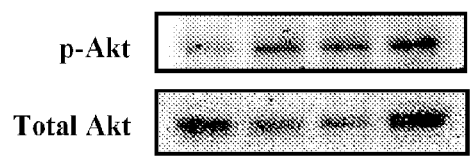
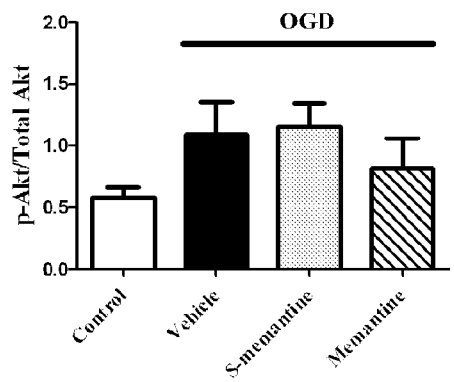
FIG. 9C
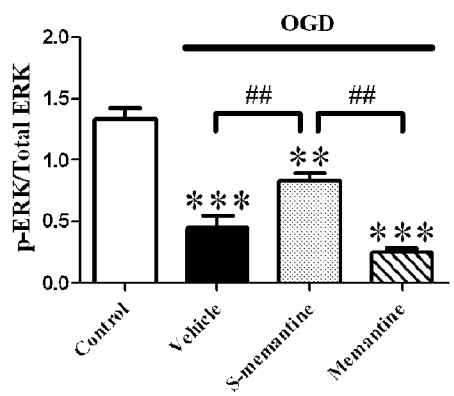

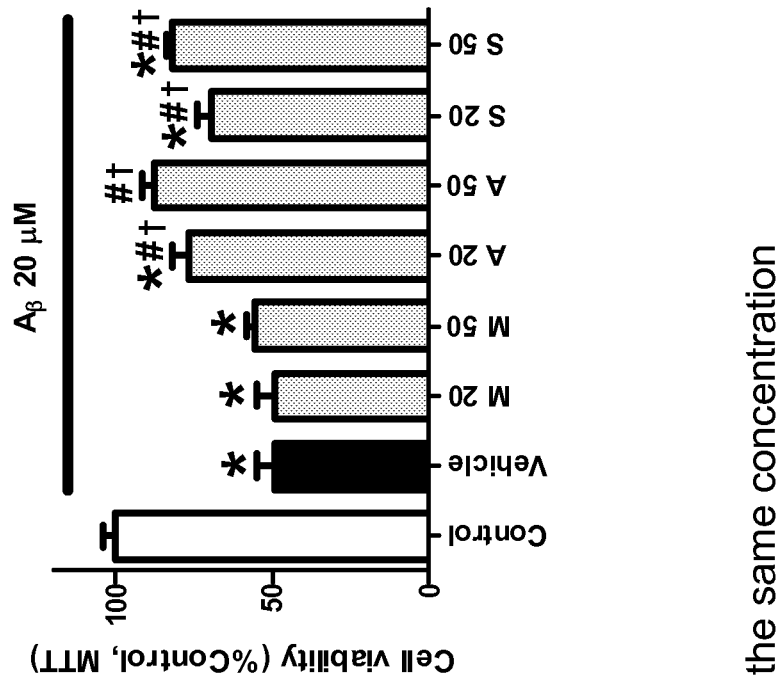
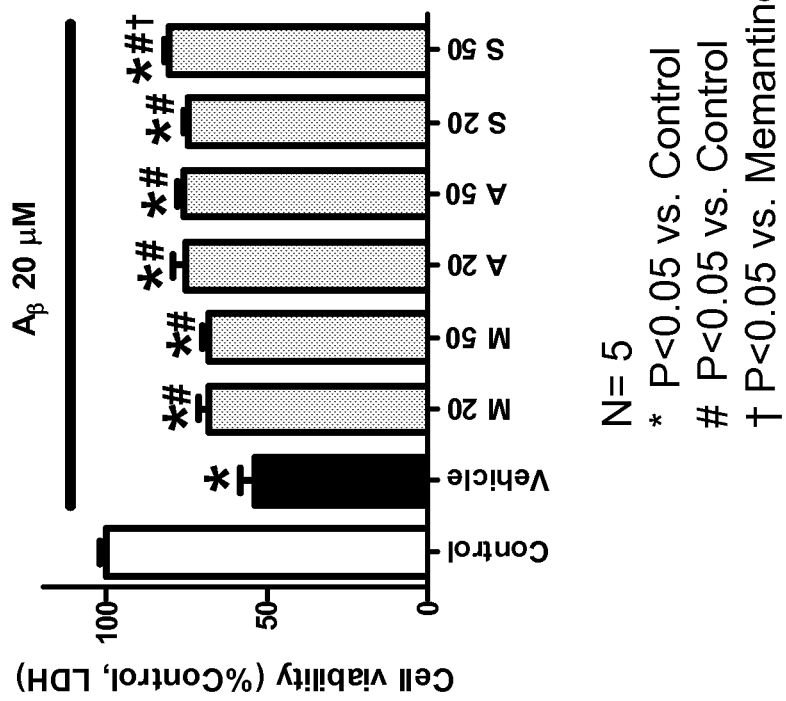
FIG. 12A
FIG. 12B
N = 5
* P<0.05 vs. Control
# P<0.05 vs. Control
† P<0.05 vs. Memantine at the same concentration N= 5
* P<0.05 vs. Control
# P<0.05 vs. Control
† P<0.05 vs. Memantine at the same concentration

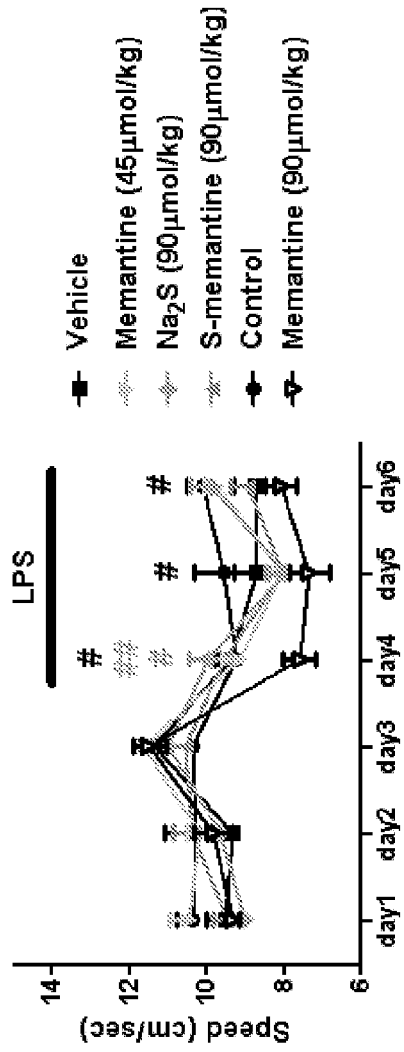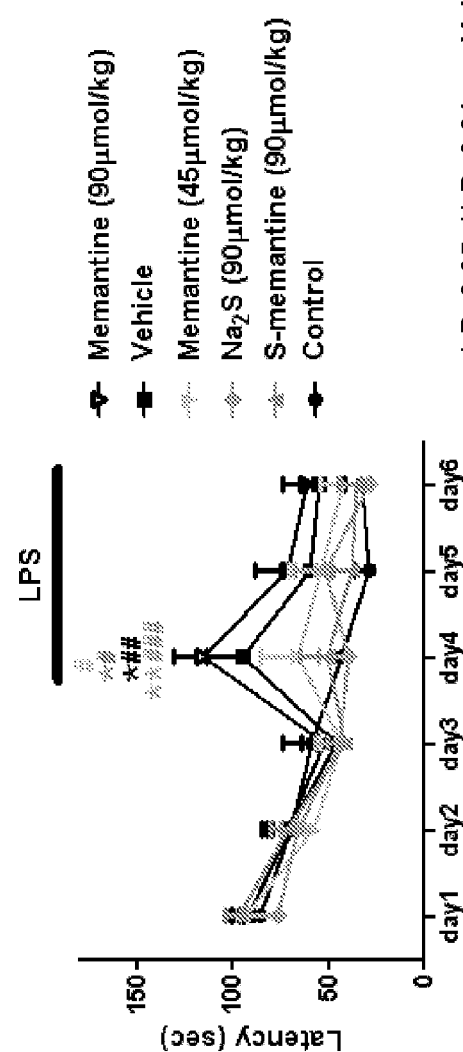

COMPOSITIONS AND METHODS TO TREAT NEURODEGENERATIVE DISEASES

FEDERALLY SPONSORED RESEARCH OR DEVELOPMENT

This invention was made with U.S. Government support under Grant Numbers R01 GM79360 awarded by The National Institute of General Medical Sciences and 1R01HL101930-01 awarded by The National Heart, Lung, and Blood Institute. The Government has certain rights in the invention.

CROSS-REFERENCE TO RELATED APPLICATIONS

This application is a U.S. National Phase Application under 35 U.S.C. §371 of International Patent Application No. PCT/US2013/050905, filed on Jul. 17, 2013, which claims priority to U.S. Provisional Application Ser. No. 61/672,533, filed on Jul. 17, 2012. The entire contents of the foregoing are hereby incorporated by reference herein.

TECHNICAL FIELD

The claimed methods and compositions relate to compositions and methods to treat neurodegenerative diseases.

BACKGROUND

Hydrogen sulfide ($H_2S$) has been proposed as a gaseous signaling molecule along with nitric oxide and carbon monoxide (Olson (2011) American Journal of Physiology—Regulatory, Integrative and Comparative Physiology 301, R297-R312). A number of studies examined therapeutic potential of $H_2S$-donating compounds and $H_2S$ gas itself for a number of animal models of human disease and injury including ischemic brain injury (Caliendo et al. (2010) J Med Chem 53, 6275-6286; Predmore et al. (2010) Journal of Cardiovascular Translational Research 3, 487-498).

Gaseous $H_2S$, however, may be difficult to be used clinically because of its characteristic odor and toxicity at high concentrations (Olson (2011) American Journal of Physiology—Regulatory, Integrative and Comparative Physiology 301, R297-R312; Reiffenstein et al. (1992) Annu Rev Pharmacol Toxicol 32, 109-134). Sodium sulfide ($Na_2S$) and sodium hydrosulfide (NaHS) have been used as $H_2S$ donor compounds in the majority of experimental studies (Caliendo et al. (2010) J Med Chem 53, 6275-6286; Predmore et al. (2010) Journal of Cardiovascular Translational Research 3, 487-498). However, because the half-lives of these sulfide salts are very short in biological fluid, plasma sulfide levels rapidly increase after bolus administration of $Na_2S$ or NaHS and then return to baseline instantaneously (DeLeon et al. (2012) Anal Biochem 421, 203-207). To sustain "physiological" levels of sulfide in circulation after bolus administration, many slow-releasing $H_2S$ donor compounds, including ACS48, have been developed (Caliendo et al. (2010) J Med Chem 53, 6275-6286; Lee et al. (2010) J Biol Chem 285, 17318-17328).

While it has been reported that low and physiological levels of $H_2S$ protect neurons, $H_2S$ also exhibits neurotoxicity especially at high concentrations (Reiffenstein et al. (1992) Annu Rev Pharmacol Toxicol 32, 109-134). Some investigators have suggested that $H_2S$-induced neurotoxicity may be mediated via enhancement of N-methyl-D-aspartate (NMDA) receptor activity (Chen et al. (2011) J Cell Physiol 226, 1308-1322; Qu et al. (2006) Stroke 37, 889-893; Cheung et al. (2007) Neuropharmacology 53, 505-514), because toxicity of $H_2S$ was abolished by NMDA receptor antagonists in vitro and in vivo (Qu et al. (2006) Stroke 37, 889-893; Cheung et al. (2007) Neuropharmacology 53, 505-514). Based on these observations, it would be desirable to deliver $H_2S$ specifically to the central nervous system with a hybrid NMDA receptor antagonist that is capable of slowly releasing $H_2S$ in circulation to treat neurodegenerative diseases.

SUMMARY

The present disclosure is based, at least in part, on the discovery that compounds comprising a sulfide donor conjugated to an NMDA receptor antagonist can be used to inhibit or reduce neuronal death. The present disclosure provides compositions and methods to treat neurodegenerative diseases, including taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria.

Accordingly, in one aspect, the present specification provides a compound comprising or consisting of a sulfide donor, e.g., ACS48, ACS5, ACS50, ACS81, 4-carbamothioylbenzoic acid, $Na_2S$, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione, conjugated to an NMDA receptor antagonist, e.g., memantine amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid (see, e.g., U.S. Pat. Nos. 5,061,703 and 8,039,009; US 2012/0004318, US 2011/0236439, US 2011/0165252, US 2011/0046232, US 2010/0081723, US 2010/0048726, and US 2006/0035888, the entire contents of which are hereby incorporated by reference).

In some embodiments, the sulfide donor comprises a moiety selected from the group consisting of: S—S—S; S—S;

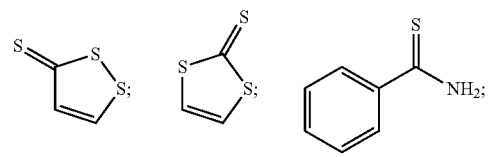

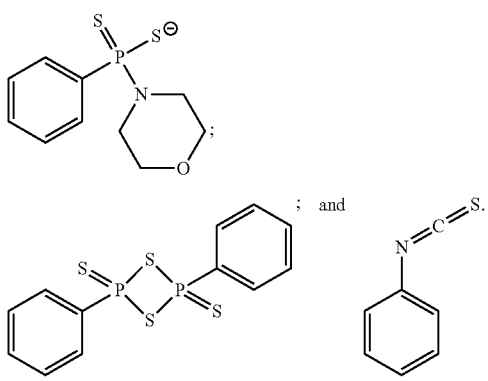

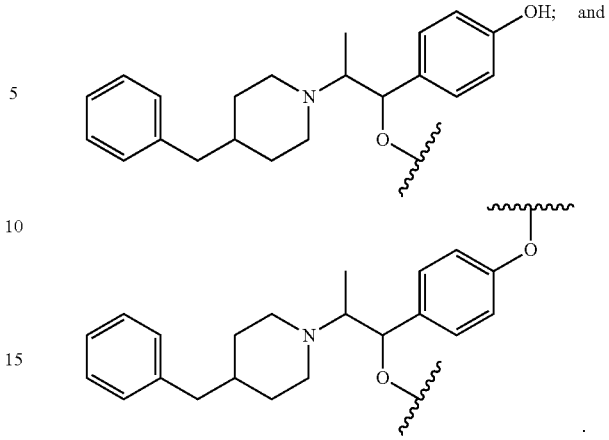

In some embodiments, the sulfide donor and the NMDA receptor antagonist are conjugated by an amide linkage, a sulfonamide linkage, a phosphoramide linkage, an ester linkage, an ether linkage, a thioether linkage, or an amine linkage.

In some embodiments, the compounds provided herein comprise or consist of a structure of Formula (I):

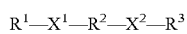

or a pharmaceutically acceptable salt thereof,
wherein:
$R^1$ is an NMDA receptor antagonist;
$X^1$ is absent or selected from the group consisting of: —NH—, —CO—, —COO—, —OCO—, —NHCO—, —CONH—, —S—, —S—S—, —S—S—S—, $(C_1-C_{20})$ alkylene; and a $(C_1-C_{20})$alkylenehalide;
$R^2$ is absent or is selected from the group consisting of: —NH—, —CO—, —COO—, —OCO—, —NHCO—, —CONH—, —S—, —S—S—, —S—S—S—, $(C_1-C_{20})$ alkylene; and a $(C_1-C_{20})$alkylenehalide;
$X^2$ is absent or selected from the group consisting of: —NH—, —CO—, —COO—, —OCO—, —NHCO—, —CONH—, —S—, —S—S—, —S—S—S—, $(C_1-C_{20})$ alkylene; and a $(C_1-C_{20})$alkylenehalide; and
$R^3$ is a sulfide donor.

In some embodiments, $R^1$ is selected from the group consisting of:

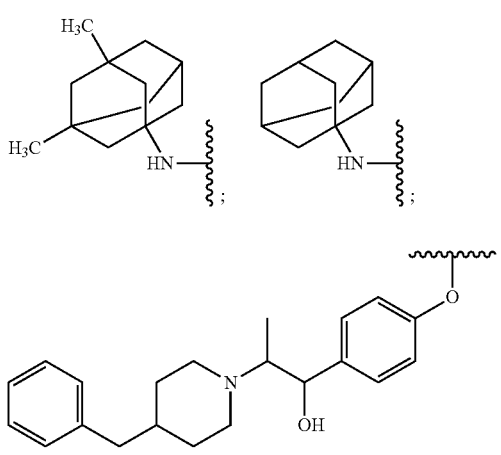

In some embodiments, $R^3$ is selected from the group consisting of:

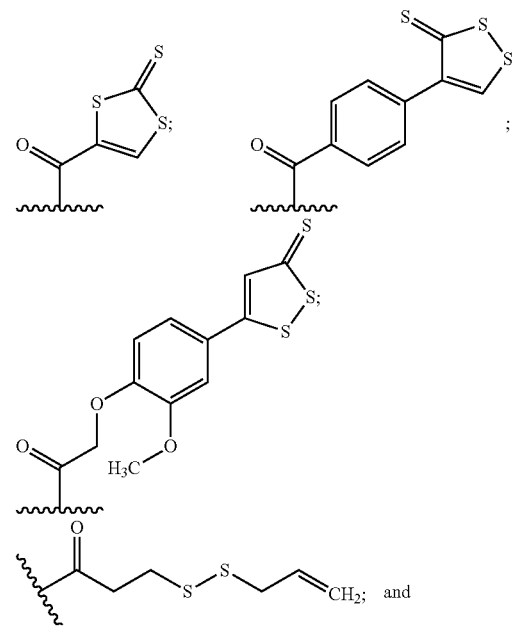

For example, in some embodiments, the compound comprises or consists of ACS48 and memantine. In some embodiments, the compound is N-((1r,3R,5S,7r)-3,5-dimethyladamantan-1-yl)-4-(3-thioxo-3H-1,2-dithiol-4-yl)-benzamide (i.e., S-memantine, which includes memantine and the sulfide donor ACS48).

In some embodiments, the compound comprises or consists of ACS5 and memantine, ACS50 and memantine, ACS81 and memantine, 4-carbamothioylbenzoic acid and memantine, ACS48 and amantadine, ACS5 and amantadine, ACS50 and amantadine, ACS81 and amantadine, 4-carbamothioylbenzoic acid and amantadine, ACS48 and ifenprodil, ACS5 and ifenprodil, ACS50 and ifenprodil, ACS81 and ifenprodil, 4-carbamothioylbenzoic acid and ifenprodil, ACS48 and ketamine, ACS5 and ketamine, ACS50 and ketamine, ACS81 and ketamine, or 4-carbamothioylbenzoic acid and ketamine.

Non-limiting examples of compounds of Formula (I) include:

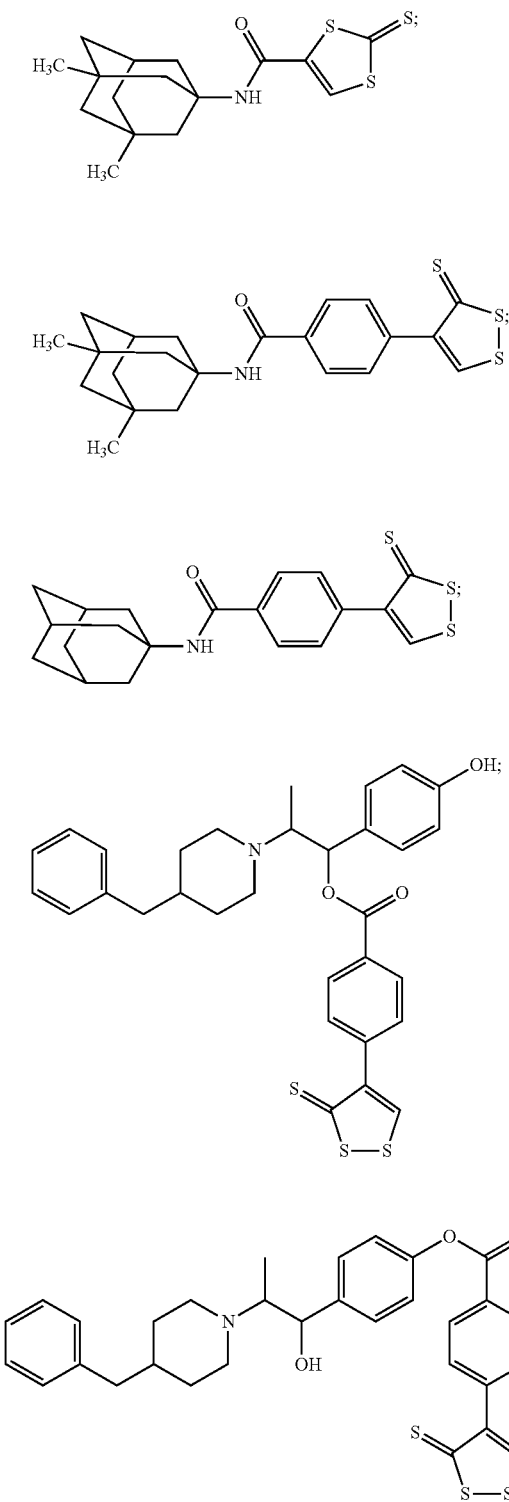

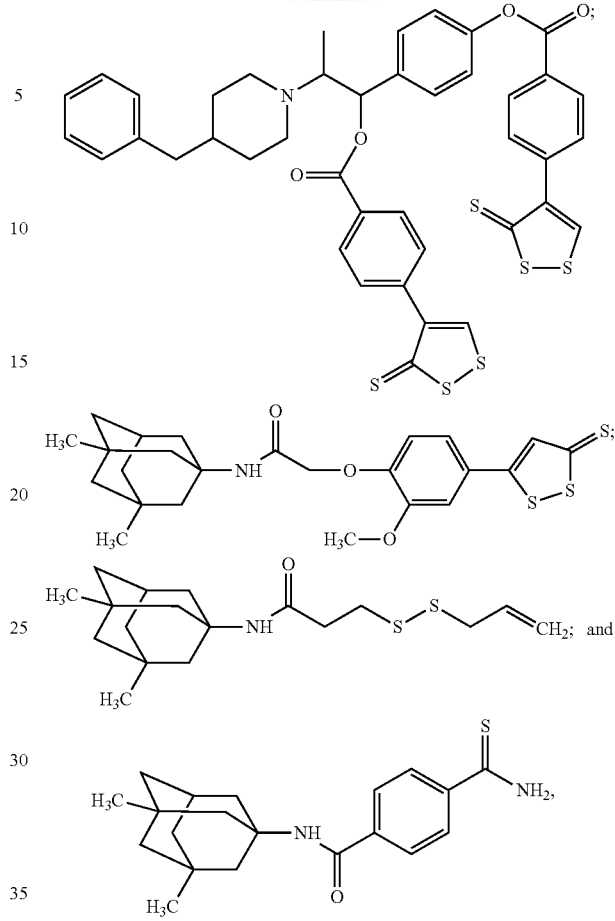

or a pharmaceutically acceptable salt thereof.

In some embodiments, pharmaceutical compositions comprise or consist of a compound comprising a sulfide donor, e.g., ACS48, ACS5, ACS50, ACS81, 4-carbamothioylbenzoic acid, Na₂S, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione, conjugated to an NMDA receptor antagonist, e.g., memantine amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid, and a pharmaceutically acceptable carrier.

In another aspect, pharmaceutical compositions comprising or consisting of a sulfide donor, an NMDA receptor antagonist, and a pharmaceutically acceptable carrier are provided. In some embodiments, the sulfide donor is ACS48, ACS5, ACS50, ACS81, 4-carbamothioylbenzoic acid, Na₂S, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, or 5-(4-hydroxyphenyl)-3H-1,2-dithiole-3-thione. In some embodiments, the NMDA receptor antagonist is memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, or pharmaceutically acceptable salts thereof.

In still another aspect, methods of treating or reducing a risk of developing a neurodegenerative disease, e.g., taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria, in a subject are described. The methods include or consist of administering to a subject a therapeutically effective amount of a compound or a pharmaceutical composition described herein, e.g., a compound or pharmaceutical composition comprising or consisting of a sulfide donor, e.g., ACS48, ACS5, ACS50, ACS81, 4-carbamothioylbenzoic acid, Na₂S, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione, conjugated or unconjugated to an NMDA receptor antagonist, e.g., memantine amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid, to treat or reduce the risk of developing a neurodegenerative disease in the subject.

The compounds and compositions provided herein can be used in the manufacture of a medicament for the treatment or reduction in the risk of developing a neurodegenerative disease, e.g., taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria, in a subject are described. A therapeutically effective amount of a compound or compositions as provided herein can be administered to a subject to treat or reduce the risk of developing a neurodegenerative disease in the subject.

In some embodiments, the compounds or pharmaceutical compositions are administered to the subject intravenously, orally, intrathecally, intraperitoneally, intramuscularly, or by implantation. In another embodiment, the methods further include administering to the subject an anti-neurodegenerative therapy, e.g., memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, an acetylcholinesterase inhibitor, tetrabenazine, benzodiazepine, levodopa, a dopamine agonist, a monoamine oxidase-B inhibitor, idebenone, riluzole, interferons, glatiramer acetate, mitoxantrone, or natalizumab.

In a further aspect, methods of synthesizing a compound comprising or consisting of a sulfide donor, e.g., ACS48, ACS5, ACS50, ACS81, 4-carbamothioylbenzoic acid, Na₂S, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione, conjugated to an NMDA receptor antagonist, e.g., memantine amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benzenesulfonic, p-toluene sulfonic, cyclohexanesulfamic, salicyclic, p-aminosalicylic, 2-phenoxybenzoic, and 2-acetoxybenzoic acid, are provided.

In some embodiments, the methods include providing a sulfide donor and an NMDA receptor antagonist and reacting the sulfide donor and the NMDA receptor antagonist under conditions sufficient to conjugate the sulfide donor and the NMDA receptor antagonist, thereby synthesizing a compound comprising or consisting of a sulfide donor conjugated to an NMDA receptor antagonist. In yet further embodiments, the methods include purifying the compound, e.g., by filtration and/or chromatography.

In some embodiments, reacting the sulfide donor and the NMDA receptor antagonist under conditions sufficient to conjugate the sulfide donor and the NMDA receptor antagonist includes forming an amide linkage, a sulfonamide linkage, a phosphoramide linkage, an ester linkage, an ether linkage, a thioether linkage, or an amine linkage. In some embodiments, the reaction is a condensation reaction, an amidation reaction, a thiol-maleimide coupling reaction, an imine formation reaction, an esterification reaction, or an etherification reaction.

In yet another embodiment, reacting the sulfide donor and the NMDA receptor antagonist includes formation of an amide linkage, wherein formation of the amide linkage includes coupling an amine moiety with a carboxylic acid moiety using a coupling agent, e.g., O-(7-azabenzotriazol-7-yl)-N,N,N',N'-tetramethyluronium hexafluorophosphate, a carbodiimide, a phosphonium-based reagent, an aminium-based reagent, or a carbonyldiimidazole.

In the methods described herein, the subject or patient can be an animal, human or non-human, and rodent or non-rodent. For example, the patient can be any mammal, e.g., a human, other primate, pig, rodent such as mouse or rat, rabbit, guinea pig, hamster, cow, horse, cat, dog, sheep or goat, or a non-mammal such as a bird.

As used herein, "conjugated" refers to the formation of a covalent bond between atoms on two individual compounds. For example, conjugation of a sulfide donor and an NMDA receptor antagonist as described herein can occur through the formation of an amide linkage, a sulfonamide linkage, a phosphoramide linkage, an ester linkage, an ether linkage, a thioether linkage, or an amine linkage between the two compounds.

The term "alkyl" includes straight-chain alkyl groups (e.g., methyl, ethyl, propyl, butyl, pentyl, hexyl, heptyl, octyl, nonyl, and decyl) and branched-chain alkyl groups (isopropyl, tert-butyl, isobutyl, and sec-butyl), cycloalkyl (alicyclic) groups (cyclopropyl, cyclopentyl, cyclohexyl, cycloheptyl, and cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain; $C_3$-$C_6$ for branched chain). The term $C_1$-$C_6$ includes alkyl groups containing 1 to 6 carbon atoms.

The term "halo" includes chloro, bromo, iodo, and fluoro.

The term "alkylene" by itself or as part of another molecule means a divalent radical derived from a linear or branched alkane, as exemplified by $(-CH_2-)_n$, wherein n may be 1 to 20 (e.g., 1 to 20, 1 to 18, 1 to 16, 1 to 15, 1 to 12, 1 to 10, 1 to 8, 1 to 6, 1 to 5, 1 to 4, 1 to 3, 1 to 2, 2 to 20, 2 to 12, 2 to 8). By way of example only, such groups include, but are not limited to, groups having 10 or fewer carbon atoms such as the structures $-CH_2CH_2-$ and $-CH_2CH_2CH_2CH_2-$. A "lower alkylene" is a shorter chain alkylene group, generally having eight or fewer carbon atoms.

The term "alkylenehalide" by itself or as part of another molecule means a divalent radical derived from a linear or branched alkane having one or more hydrogens on the alkane independently replaced with a halo.

As used herein, a "linker moiety" is any group of atoms that connects two individual compounds via covalent bonds. For example, a linker moiety can be used to covalently attach a sulfide donor to an NMDA receptor antagonist. The linker moiety may be include $-COO-$, $-OCO-$, $-NHCO-$, $-CONH-$, $-S-$, $-S-S-$, $-S-S-S-$, $(C_1$-$C_{20})$ alkylene; or $(C_1$-$C_{20})$alkylenehalide.

As used herein, treating a neurodegenerative disease in a subject means to ameliorate at least one or more symptoms of a neurodegenerative disease. In one aspect, the disclosure features methods of treating, e.g., reducing severity or progression of, a neurodegenerative disease in a subject. The methods can include selecting a subject on the basis that they have been diagnosed with a neurodegenerative disease, or a subject with an underlying neurodegenerative disease. Selection of a subject can include detecting symptoms of a neurodegenerative disease, taking a blood test (e.g., a genetic test), or imaging tests of the brain. If the results of the test(s) indicate that the subject has a neurodegenerative disease, the methods also include administering a therapeutically effective amount of a compound comprising or consisting of a sulfide donor conjugated or unconjugated to an NMDA receptor antagonist, and detecting an effect of the compound in the subject, thereby treating a neurodegenerative disease in the subject.

Also provided herein are methods of reducing a risk of developing a neurodegenerative disease in a subject. The methods can include selecting a subject on the basis that they are at risk of developing a neurodegenerative disease, but do not yet have a neurodegenerative disease. Selection of a subject can include taking a blood test (e.g., a genetic test), reviewing a family history of a neurodegenerative disease, or imaging tests of the brain. If the results of the test(s) indicate that the subject is at risk of developing a neurodegenerative disease, the methods also include administering a therapeutically effective amount of a compound comprising or consisting of a sulfide donor conjugated or unconjugated to an NMDA receptor antagonist, and detecting an effect of the compound in the subject, thereby reducing the risk of developing a neurodegenerative disease in the subject.

As used herein, the term "neurodegenerative disease" refers to a condition having a pathophysiological component of neuronal death. Neurodegeneration is the umbrella term for the progressive loss of structure and/or function of neurons, including death of neurons. Examples of such diseases include, but are not limited to, taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria. These examples of neurodegenerative diseases and their symptoms are well-known in the art and are described in further detail below. Subjects can be diagnosed as having a neurodegenerative disease by a health care provider, medical caregiver, physician, nurse, family member, or acquaintance, who recognizes, appreciates, acknowledges, determines, concludes, opines, or decides that the subject has a neurodegenerative disease.

The term "Alzheimer's Disease" refers to a progressive mental deterioration manifested by memory loss, confusion and disorientation beginning in late middle life and typically resulting in death in five to ten years. Pathologically, Alzheimer's Disease can be characterized by thickening, conglutination, and distortion of the intracellular neurofibrils, neurofibrillary tangles and senile plaques composed of granular or filamentous argentophilic masses with an amyloid core. Methods for diagnosing Alzheimer's Disease are known in the art. For example, the National Institute of Neurological and Communicative Disorders and Stroke-Alzheimer's Disease and the Alzheimer's Disease and Related Disorders Association (NINCDS-ADRDA) criteria can be used to diagnose Alzheimer's Disease (McKhann et al., Neurology 34:939-944, 1984). The subject's cognitive function can be assessed by the Alzheimer's Disease Assessment Scale-cognitive subscale (ADAS-cog; Rosen et al., Am J Psychiatry 141:1356-1364, 1984).

The term "Huntington's Disease" refers to a neurodegenerative genetic disorder that affects muscle coordination and leads to cognitive decline and psychiatric problems. It typically becomes noticeable in mid-adult life. Huntington's Disease is the most common genetic cause of abnormal involuntary writhing movements called chorea. Symptoms of Huntington's disease commonly become noticeable between the ages of 35 and 44 years, but they can begin at any age from infancy to old age. In the early stages, there are subtle changes in personality, cognition, and physical skills. The physical symptoms are usually the first to be noticed, as cognitive and psychiatric symptoms are generally not severe enough to be recognized on their own at the earlier stages. Almost everyone with Huntington's Disease eventually exhibits similar physical symptoms, but the onset, progression and extent of cognitive and psychiatric symptoms vary significantly between individuals. The most characteristic initial physical symptoms are jerky, random, and uncontrollable movements called chorea. Chorea may be initially exhibited as general restlessness, small unintentionally initiated or uncompleted motions, lack of coordination, or slowed saccadic eye movements. These minor motor abnormalities usually precede more obvious signs of motor dysfunction by at least three years. The clear appearance of symptoms such as rigidity, writhing motions or abnormal posturing appear as the disorder progresses. These are signs that the system in the brain that is responsible for movement has been affected. Psychomotor functions become increasingly impaired, such that any action that requires muscle control is affected. Common consequences are physical instability, abnormal facial expression, and difficulties chewing, swallowing and speaking. Eating difficulties commonly cause weight loss and may lead to malnutrition. Sleep disturbances are also associated symptoms.

The term "Parkinson's Disease" refers to a disorder of the brain that leads to shaking (tremors) and difficulty with walking, movement, and coordination. Parkinson's Disease most often develops after age 50. It is one of the most common nervous system disorders of the elderly. It affects both men and women. In some cases, Parkinson's Disease runs in families. When a young person is affected, it is usually because of a form of the disease that runs in families. There are currently no known cures for Parkinson's Disease. The goal of treatment is to control symptoms. Nerve cells use a brain chemical called dopamine to help control muscle movement. Parkinson's Disease occurs when the nerve cells in the brain that make dopamine are slowly destroyed. Without dopamine, the nerve cells in that part of the brain cannot properly send messages. This leads to the loss of muscle function. The damage gets worse with time. Exactly why these brain cells waste away is unknown.

The term "Friedreich's ataxia" refers to an inherited disease that causes progressive damage to the nervous system, resulting in symptoms ranging from gait disturbance to speech problems; it can also lead to heart disease and diabetes. The ataxia of Friedreich's ataxia results from the degeneration of nerve tissue in the spinal cord, in particular sensory neurons essential (through connections with the cerebellum) for directing muscle movement of the arms and legs. The spinal cord becomes thinner and nerve cells lose some of their myelin sheath (the insulating covering on some nerve cells that helps conduct nerve impulses).

The term "amyotrophic lateral sclerosis" or "ALS" also known as Lou Gehrig's disease, refers to a disease of the nerve cells in the brain and spinal cord that control voluntary muscle movement. In ALS, neurons waste away or die, and can no longer send messages to muscles. This eventually leads to muscle weakening, twitching, and an inability to move the arms, legs, and body. The condition slowly gets worse. When the muscles in the chest area stop working, it becomes hard or impossible to breathe on one's own. ALS affects approximately 5 out of every 100,000 people worldwide. There are no known risk factors, except for having a family member who has a hereditary form of the disease. Symptoms usually do not develop until after age 50, but they can start in younger people. Persons with ALS have a loss of muscle strength and coordination that eventually gets worse and makes it impossible to do routine tasks such as going up steps, getting out of a chair, or swallowing. Breathing or swallowing muscles may be the first muscles affected. As the disease gets worse, more muscle groups develop problems. ALS does not affect the senses (sight, smell, taste, hearing, touch). It only rarely affects bladder or bowel function, or a person's ability to think or reason.

The term "multiple sclerosis" refers to a disease caused by damage to the myelin sheath, the protective covering that surrounds neurons. When this nerve covering is damaged, nerve signals slow down or stop. The nerve damage is caused by inflammation. Inflammation occurs when the body's own immune cells attack the nervous system. This can occur along any area of the brain, optic nerve, and spinal cord. It is unknown what exactly causes this to happen. The most common thought is that a virus or gene defect, or both, are to blame. Environmental factors may play a role. Symptoms vary, because the location and severity of each attack can be different. Episodes can last for days, weeks, or months. These episodes alternate with periods of reduced or no symptoms (remissions). Fever, hot baths, sun exposure, and stress can trigger or worsen attacks. It is common for the disease to return (relapse). However, the disease may continue to get worse without periods of remission. Because nerves in any part of the brain or spinal cord may be damaged, patients with multiple sclerosis can have symptoms in many parts of the body.

The term "ischemic brain injury" refers to a condition in which there is insufficient blood flow to the brain to meet metabolic demand. This leads to poor oxygen supply or cerebral hypoxia and thus to the death of brain tissue or cerebral infarction/ischemic stroke. It is a sub-type of stroke along with subarachnoid hemorrhage and intracerebral hemorrhage. Ischemic brain injury leads to alterations in brain metabolism, reduction in metabolic rates, and energy crisis. There are two types of ischemia: focal ischemia, which is confined to a specific region of the brain; and global ischemia, which encompasses wide areas of brain tissue. The main symptoms involve impairments in vision, body movement, and speaking. The causes of ischemic brain injury vary from sickle cell anemia to congenital heart defects. Symptoms of ischemic brain injury can include unconsciousness, blindness, problems with coordination, and weakness in the body. Other effects that may result from brain ischemia are stroke, cardiorespiratory arrest, and irreversible brain damage.

Reperfusion injury results from the brain's ischemic cascade, which is involved in stroke and brain trauma. Similar failure processes are involved in brain failure following reversal of cardiac arrest; control of these processes is the subject of ongoing research. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

The term "glaucoma" refers to a group of eye conditions that lead to damage to the optic nerve. In most cases, damage to the optic nerve is due to increased pressure in the eye, also known as intraocular pressure. Glaucoma is the second most common cause of blindness in the United States. The front part of the eye is filled with a clear fluid called aqueous humor. This fluid is always being made behind the iris. It leaves the eye through channels in the front of the eye in an area called the anterior chamber angle. Anything that slows or blocks the flow of this fluid out of the eye will cause pressure to build up in the eye. In most cases of glaucoma, this pressure is high and causes damage to the optic nerve.

The term "sulfide" as used herein is not necessarily limited to the particular species $H_2S$, but includes the sulfide species $H_2S$, $HS^-$, $S^{-2}$, and sulfide donor molecules, unless otherwise specified.

The term "NMDA receptor antagonists" as used herein refers to a class of compounds that work to antagonize, or inhibit the action of, the NMDA receptor and includes, but is not necessarily limited to memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid (see, e.g., U.S. Pat. Nos. 5,061,703 and 8,039,009; US 2012/0004318, US 2011/0236439, US 2011/0165252, US 2011/0046232, US 2010/0081723, US 2010/0048726, and US 2006/0035888, the entire contents of which are hereby incorporated by reference).

Unless otherwise defined, all technical terms used herein have the same meaning as commonly understood by one of ordinary skill in the art to which this disclosure belongs. While various methods and materials are described herein, other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-E is a series of four bar graphs and a photograph showing the effects of $H_2S$ donors and memantine on cell viability after OGD. (A-D) ACS48, memantine, and S-memantine at 50 µM or vehicle was added 8 hours after the end of OGD. LDH released in the culture medium was measured 24 hours after the end of OGD. (A) LDH-release from SH-SY5Y after OGD. N=5 or 6 each. * $P<0.001$ vs. vehicle, # $P<0.05$. (B) MTT assay. N=5 or 6 each. No OGD control (control) differs significantly from all other groups ($P<0.001$). * $P<0.01$ vs. vehicle, # $P<0.05$. (C) CV assay and (D) photographs of wells containing SH-SY5Y stained with CV after OGD. N=5 each. No OGD control (control) differs significantly from all other groups ($P<0.001$), * $P<0.001$ vs. vehicle, # $P<0.05$. (E) LDH released from murine primary cortical neurons measured 2.5 hours after the end of OGD. ACS48, memantine, and S-memantine at 50 µM or vehicle was added 0.5 hours after the end of OGD. LDH released in the culture medium was measured 21 hours after the end of OGD. N=5 or 6 each. * $P<0.001$ vs. vehicle, # $P<0.001$ vs. ACS48 and memantine.

FIGS. 9A-C is a series of photomicrographs and bar graphs depicting representative immunoblot and densitometric analysis of (A) cleaved caspase-3, (B) phosphorylated Akt (p-Akt), and (C) phosphorylated extracellular-signal regulated kinase 1/2 (p-ERK) protein expression in SH-SY5Y after 15 hours of OGD and 24 hours of reoxygenation with or without the addition of S-memantine or memantine at 50 µM at 8 hours after the end of OGD. Relative intensity was normalized to total caspase-3, total Akt, or total ERK, respectively. N=3 or 4 each.  P<0.01, or * P<0.001 vs. control. # P<0.05, ## P<0.01.

FIG. 12A-B is a set of two bar graphs showing cell viability of SH-SY5Y cells exposed to 20 µM amyloid beta (Aβ) and treated with memantine, ACS48, or S-memantine at 20 or 50 µM. Cell viability was estimated by LDH release assay in the left graph and MTT assay in the right graph.

FIG. 15A-B is a series of two line graphs depicting the results from a Morris water-maze test in the LPS-induced cognitive dysfunction model. The upper panel shows swimming speed and the lower panel shows the latency to escape in mice challenged with LPS and treated with vehicle, memantine, Na2S, or S-memantine. Control mice had no LPS.

DETAILED DESCRIPTION

Figure 1A:
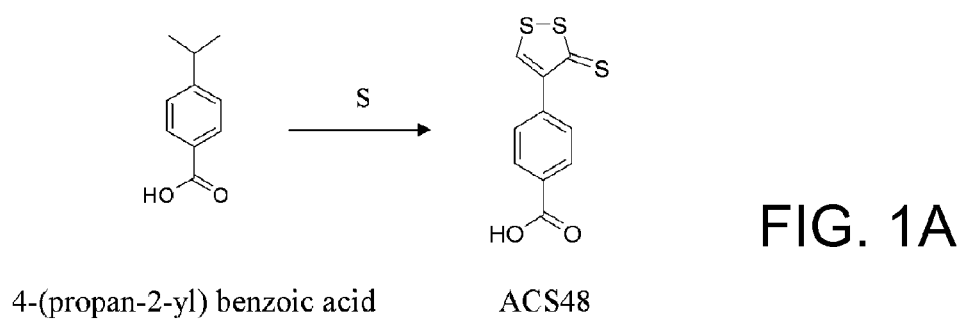
FIGS. 1A-C are schematic diagrams of synthesis of (A) ACS48, (B)S-memantine, and (C) ACS5-memantine, ACS48-memantine, ACS50-memantine, ACS81-memantine, CTBA-memantine, ACS48-amantadine, and ACS48-ifenprodil compounds.

Provided herein are newly-synthesized H$_2$S-releasing NMDA receptor antagonist compounds, e.g., S-memantine, which increase intracellular H$_2$S levels to protect neurons from degeneration more robustly than conventional H$_2$S donor compounds (e.g., Na$_2$S and ACS48) and cause less cyotoxicity. The compounds retain the beneficial effects of the NMDA receptor antagonist, e.g., memantine, and reduce glutamate-induced intracellular calcium accumulation. Post-reperfusion treatment with S-memantine attenutates cerebral injury induced by global cerebral ischemia and reperfusion in mice. The present H$_2$S-releasing NMDA receptor antagonists can be used to treat or reduce a risk of developing a neurodegenerative disease, including ischemic brain injury, taupathies (e.g., Alzheimer's Disease), Huntington's Disease, Parkinson's Disease, Friedreich's ataxia, amyotrophic lateral sclerosis, multiple sclerosis, and glaucoma, and encephalitis-, meningitis-, and trauma-induced inflammatory neuronal damage, e.g., malaria encephalitis or cerebral malaria.

Compounds

Provided herein are compounds that include a sulfide donor conjugated to a N-methyl-D-aspartate (NMDA) receptor antagonist. The sulfide donor can be conjugated either directly or indirectly (e.g., via a linker) to the NMDA receptor antagonist.

In some embodiments, the compounds can have a structure of Formula (I):

or a pharmaceutically acceptable salt thereof, wherein:
R$^1$ is an NMDA receptor antagonist;
X$^1$ is absent or selected from the group consisting of: —NH—, —CO—, —COO—, —OCO—, —NHCO—, —CONH—, —S—, —S—S—, —S—S—S—, (C$_1$-C$_{20}$) alkylene; and a (C$_1$-C$_{20}$)alkylenehalide;
R$^2$ is absent or is selected from the group consisting of: —NH—, —CO—, —COO—, —OCO—, —NHCO—, —CONH—, —S—, —S—S—, —S—S—S—, (C$_1$-C$_{20}$) alkylene; and a (C$_1$-C$_{20}$)alkylenehalide;
X$^2$ is absent or selected from the group consisting of: —NH—, —CO—, —COO—, —OCO—, —NHCO—, —CONH—, —S—, —S—S—, —S—S—S—, (C$_1$-C$_{20}$) alkylene; and a (C$_1$-C$_{20}$)alkylenehalide; and
R$^3$ is a sulfide donor.

In some embodiments, the compounds can have a structure of Formula (II) or Formula (III):

or a pharmaceutically acceptable salt thereof, wherein:
each $R^1$ is independently an NMDA receptor antagonist;
each $X^1$ is independently absent or selected from the group consisting of: —NH—, —CO—, —COO—, —OCO—, —NHCO—, —CONH—, —S—, —S—S—, —S—S—S—, $(C_1$-$C_{20})$alkylene; and a $(C_1$-$C_{20})$alkylenehalide;
each $R^2$ is independently absent or is selected from the group consisting of: —NH—, —CO—, —COO—, —OCO—, —NHCO—, —CONH—, —S—, —S—S—, —S—S—S—, $(C_1$-$C_{20})$alkylene; and a $(C_1$-$C_{20})$alkylenehalide;
each $X^2$ is independently absent or selected from the group consisting of: —NH—, —CO—, —COO—, —OCO—, —NHCO—, —CONH—, —S—, —S—S—, —S—S—S—, $(C_1$-$C_{20})$alkylene; and a $(C_1$-$C_{20})$alkylenehalide;
each $R^3$ is independently a sulfide donor; and
n and m are independently integers from 1 to 3.

The moiety $X^1$—$R^2$—$X^2$ can be a linker moiety. In some embodiments, if $R^2$ is absent, then at least one of $X^1$ and $X^2$ is absent. In some embodiments, if $X^1$ is selected from the group consisting of —COO—, —OCO—, —NHCO—, —CONH—, —S—, —S—S—, —S—S—S—, then $R^2$ is absent and $X^2$ is absent or selected from the group consisting of $(C_1$-$C_{20})$alkylene; and a $(C_1$-$C_{20})$alkylenehalide. In some embodiments, if $X^2$ is selected from the group consisting of —COO—, —OCO—, —NHCO—, —CONH—, —S—, —S—S—, —S—S—S—, then $R^2$ is absent and $X^1$ is absent or selected from the group consisting of $(C_1$-$C_{20})$alkylene; and a $(C_1$-$C_{20})$alkylenehalide. In some embodiments, if $R^2$ is selected from the group consisting of —COO—, —OCO—, —NHCO—, —CONH—, —S—, —S—S—, —S—S—S—, then $X^1$ and $X^2$ are independently absent or selected from the group consisting of $(C_1$-$C_{20})$alkylene; and a $(C_1$-$C_{20})$alkylenehalide. In some embodiments, $X^1$ is absent. In some embodiments, $X^2$ is absent. In some embodiments, $R^2$ is absent. In some embodiments, $X^1$, $X^2$, and $R^2$ are absent.

In some embodiments, m is 2. In some embodiments, m is 1. In some embodiments, n is 2. In some embodiments, n is 3.

NMDA receptor antagonists ($R^1$) include compounds that work to antagonize, or inhibit the action of, the N-Methyl-D-aspartate receptor (NMDAR). Non-limiting examples of such compounds include memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid (see, e.g., U.S. Pat. Nos. 5,061,703 and 8,039,009; US 2012/0004318, US 2011/0236439, US 2011/0165252, US 2011/0046232, US 2010/0081723, US 2010/0048726, and US 2006/0035888, the entire contents of which are hereby incorporated by reference). In some embodiments, the NMDA receptor antagonist is memantine.

In some embodiments, the NMDA receptor antagonist of moiety $R^1$ can be selected from the group consisting of:

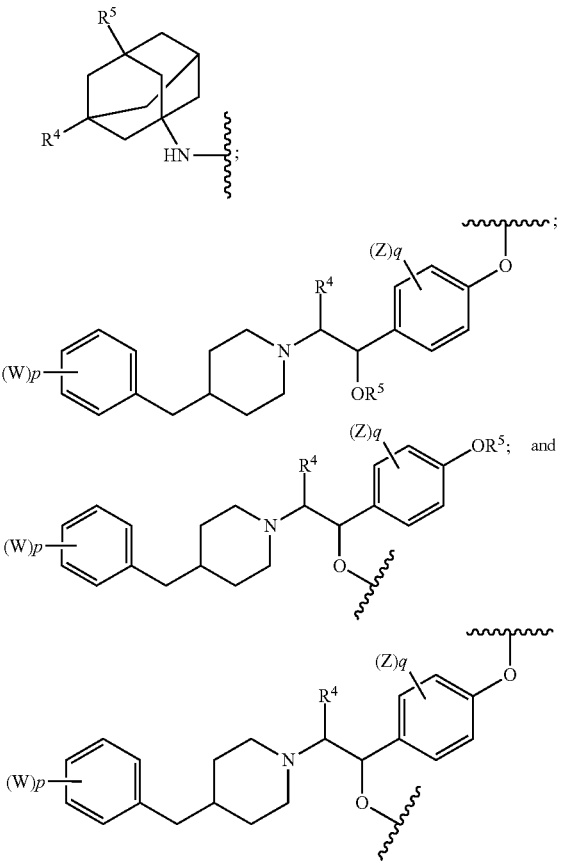

wherein:
each $R^4$ and $R^5$ is independently selected from H and $(C_1$-$C_{10})$alkyl;

each W is independently selected from the group consisting of: halo, $(C_1$-$C_6)$alkyl, $(C_1$-$C_6)$haloalkyl, —O$(C_1$-$C_6)$alkyl, and —C(O)$R^6$;

each Z is independently selected from the group consisting of: halo, $(C_1$-$C_6)$alkyl, $(C_1$-$C_6)$haloalkyl, —O$(C_1$-$C_6)$alkyl, and —C(O)$R^6$;

each $R^6$ is selected from the group consisting of: hydrogen and $(C_1$-$C_6)$alkyl;

each p is an integer from 0 to 5; and each q is an integer from 0 to 4.

In some embodiments, each $R^4$ and $R^5$ is independently selected from H and $CH_3$. In some embodiments, p and q are 0.

For example, $R^1$ can be selected from the group consisting of:

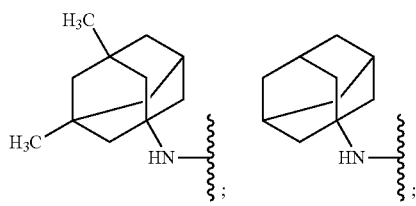

-continued

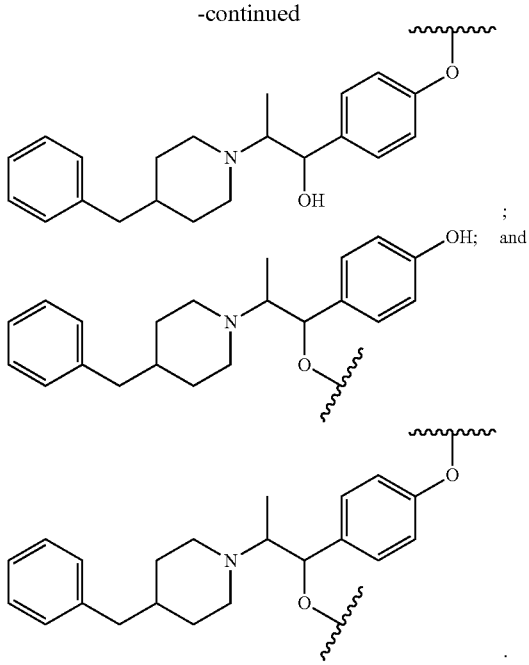

Sulfide donors (R³) can include any compound having a sulfide moiety as defined herein. For example, sulfide donors can include a moiety selected from the group consisting of: S—S—S; S—S;

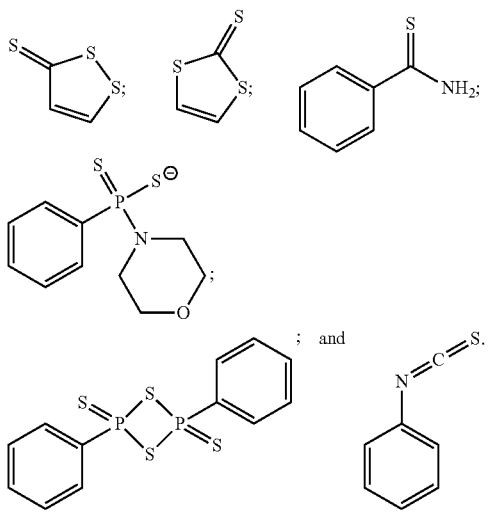

Non-limiting examples of sulfide donors include ACS48 (4-(3-thioxo-3H-1,2-dithiol-4-yl)-benzoic acid), ACS5 (1,3-dithiole-2-thioxo-4-carboxylic acid), ACS50 (([2-methoxy-4-(3-thioxo-3H-1,2-dithiol-5-yl)-phenoxy]acetic acid), ACS81 (3-(prop-2-en-1-yldisulfanyl)propanoic acid), 4-carbamothioylbenzoic acid, Na₂S, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione, and pharmaceutically acceptable salts thereof, e.g., addition salts of free acids or free bases and acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid. In some embodiments, the sulfide donor is ACS48.

In some embodiments, the sulfide donor moiety R³ can be selected from the group consisting of:

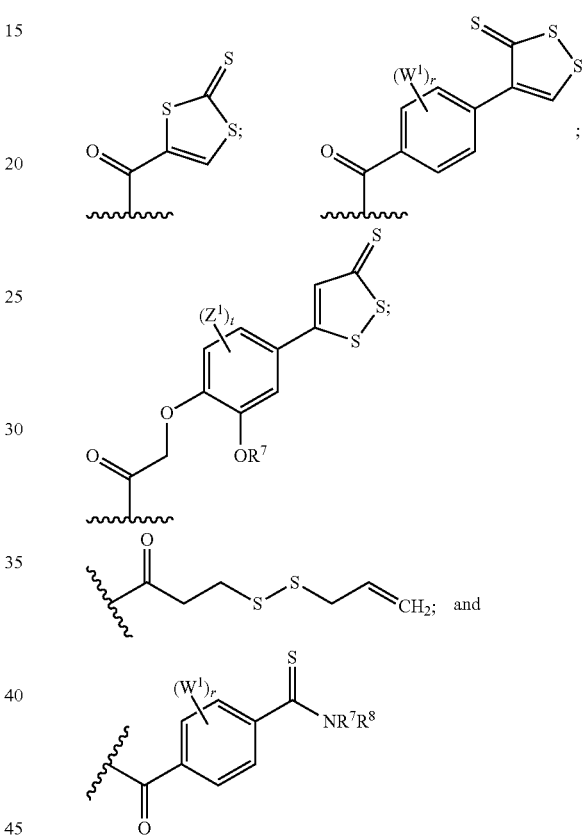

wherein:

each R⁷ and R⁸ is independently selected from H and $(C_1-C_{10})$alkyl;

each $W^1$ is independently selected from the group consisting of: halo, $(C_1-C_6)$alkyl, $(C_1-C_6)$haloalkyl, —O$(C_1-C_6)$alkyl, and —C(O)R⁹;

each $Z^1$ is independently selected from the group consisting of: halo, $(C_1-C_6)$alkyl, $(C_1-C_6)$haloalkyl, —O$(C_1-C_6)$alkyl, and —C(O)R⁹;

each R⁹ is selected from the group consisting of: hydrogen and $(C_1-C_6)$alkyl;

each r is an integer from 0 to 4; and each t is an integer from 0 to 3.

In some embodiments, each R⁷ and R⁸ is independently selected from H and CH₃. In some embodiments, r and t are 0.

For example, the sulfide donor moiety R³ can be selected from the group consisting of:

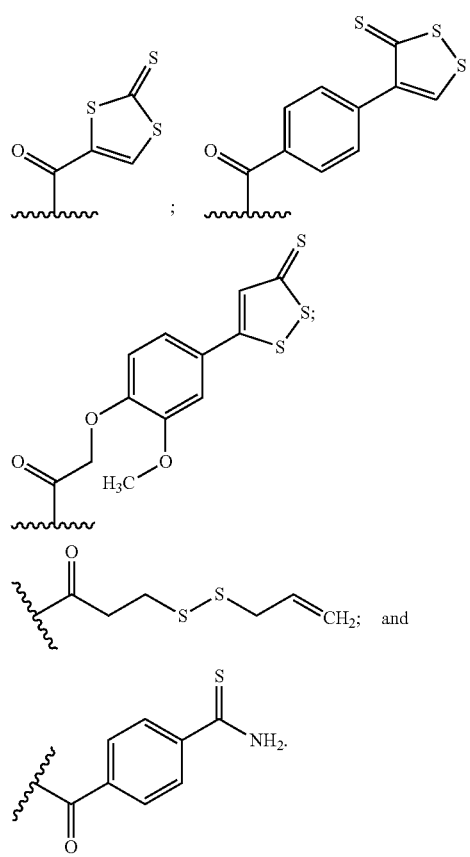

In some embodiments, the sulfide donor is ACS48 and the NMDA receptor antagonist is memantine. In some embodiments, the compound is N-((1r,3R,5S,7r)-3,5-dimethyladamantan-1-yl)-4-(3-thioxo-3H-1,2-dithiol-4-yl)-benzamide (S-memantine).

Non-limiting examples of a compound provided herein (e.g., a compound of Formula (I)) include:

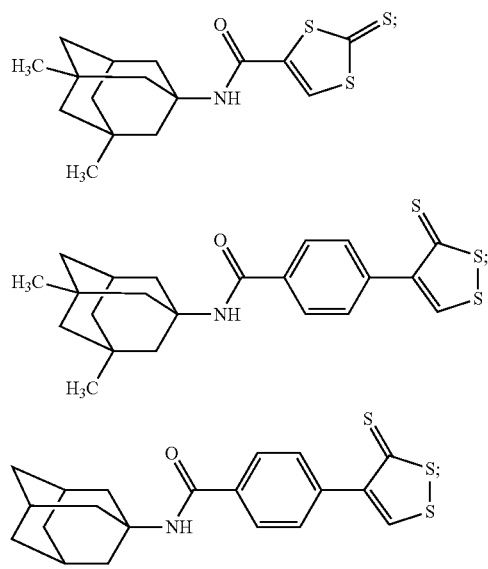

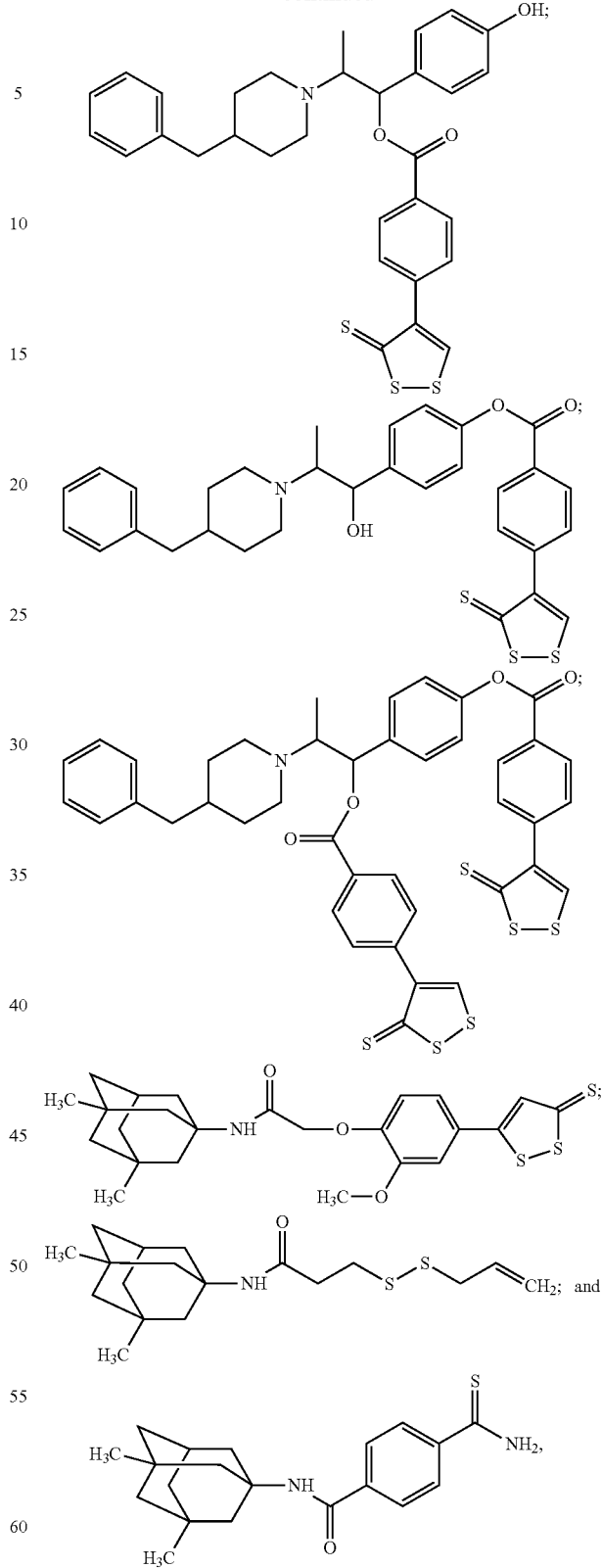

or a pharmaceutically acceptable salt thereof.

The compounds (e.g., a compound of Formula (I)) can be synthesized by reacting a sulfide donor with a NMDA receptor antagonist through a chemical reaction. Skilled practitioners will appreciate that such compounds can be synthesized in any number of ways, e.g., a condensation reaction, an amidation reaction, a thiol-maleimide coupling reaction, an imine formation reaction, an esterification reaction, or an etherification reaction, to form an amide linkage, a sulfonamide linkage, a phosphoramide linkage, an ester linkage, an ether linkage, a thioether linkage, or an amine linkage between the sulfide donor and the NMDA receptor antagonist.

For example, the sulfide donor ACS48 can be conjugated by an amide linkage to the NMDA receptor antagonist memantine to form N-((1r,3R,5S,7r)-3,5-dimethyladamantan-1-yl)-4-(3-thioxo-3H-1,2-dithiol-4-yl)-benzamide (i.e., S-memantine, which includes memantine and the sulfide donor ACS48). Nonetheless, skilled practitioners will appreciate that ACS48 can be substituted with a sulfur-containing compound with a moiety such as those illustrated below. Examples of sulfide donors include ACS5, ACS50, ACS81, 4-carbamothioylbenzoic acid, sulfide salts (e.g., $Na_2S$, NaHS, potassium sulfide, potassium hydrosulfide, magnesium sulfide, and calcium sulfide), sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione.

The compounds comprising or consisting of, e.g., ACS48 and memantine, ACS5 and memantine, ACS50 and memantine, ACS81 and memantine, 4-carbamothioylbenzoic acid and memantine, ACS48 and amantadine, ACS5 and amantadine, ACS50 and amantadine, ACS81 and amantadine, 4-carbamothioylbenzoic acid and amantadine, ACS48 and ifenprodil, ACS5 and ifenprodil, ACS50 and ifenprodil, ACS81 and ifenprodil, 4-carbamothioylbenzoic acid and ifenprodil, ACS48 and ketamine, ACS5 and ketamine, ACS50 and ketamine, ACS81 and ketamine, or 4-carbamothioylbenzoic acid and ketamine, can be purified by known methods in the art, e.g., filtration and chromatography. "Purified" refers to a compound that is substantially free of chemical precursors or other chemicals (when chemically synthesized). A purified compound is a composition that is at least 75% by weight the compound of interest, e.g., S-memantine. In general, the preparation is at least 80% (e.g., at least 90%, 95%, 96%, 97%, 98%, 99%, or 100%) by weight the compound of interest. Purity can be measured by any appropriate standard method, e.g., mass spectrometry and NMR spectrometry.

Pharmaceutical Compositions

Also described herein are pharmaceutical compositions, which include (e.g., comprise or consist of) the $H_2S$-releasing NMDA receptor antagonist compounds described herein (e.g., compounds of Formula (I)). Exemplary pharmaceutical compositions include or consist of compounds comprising, e.g., ACS48 and memantine, ACS5 and memantine, ACS50 and memantine, ACS81 and memantine, 4-carbamothioylbenzoic acid and memantine, ACS48 and amantadine, ACS5 and amantadine, ACS50 and amantadine, ACS81 and amantadine, 4-carbamothioylbenzoic acid and amantadine, ACS48 and ifenprodil, ACS5 and ifenprodil, ACS50 and ifenprodil, ACS81 and ifenprodil, 4-carbamothioylbenzoic acid and ifenprodil, ACS48 and ketamine, ACS5 and ketamine, ACS50 and ketamine, ACS81 and ketamine, or 4-carbamothioylbenzoic acid and ketamine, wherein the sulfide donor is conjugated as described herein to the NMDA receptor antagonist. In another aspect, the sulfide donor is not conjugated to the NMDA receptor antagonist.

Pharmaceutical compositions typically include or consist of the active compound or compounds and a pharmaceutically acceptable carrier. A "pharmaceutically acceptable carrier" means any carrier, diluent or excipient which is compatible with the other ingredients of the formulation and not deleterious to the recipient. For preparing pharmaceutical compositions as provided herein, inert, pharmaceutically acceptable carriers can be either solid or liquid. Solid form preparations include powders, tablets, dispersible granules, capsules, cachets, and suppositories. A solid carrier can be one or more substances that may also act as diluents, flavoring agents, solubilizers, lubricants, suspending agents, binders, or tablet disintegrating agents; it can also be an encapsulating material. In powders, the carrier is a finely divided solid which is in admixture with the finely divided active compounds of the present invention. In the tablet the active compound is mixed with carrier having the necessary binding properties in suitable proportions and compacted in the shape and size desired. The powders and tablets can contain from 5% to 10% to about 70% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. Similarly, cachets are included. Tablets, powders, cachets, and capsules can be used as solid dosage forms suitable for oral administration.

Liquid formulations include solutions, suspensions, and emulsions. As an example, water or water-propylene glycol solutions may be mentioned for parenteral injections. Liquid preparations can also be formulated in solution in aqueous polyethylene glycol solution. Aqueous solutions suitable for oral use can be prepared by dissolving a compound as provided herein in water and adding suitable colorants, flavors, stabilizing, and thickening agents as desired. Aqueous suspensions suitable for oral use can be made by dispersing the finely divided compound in water with viscous material, i.e., natural or synthetic gums, resins, methyl cellulose, sodium carboxymethyl cellulose, and other well-known suspending agents.

Supplementary active compounds can also be incorporated into the compositions. The pharmaceutical compositions can be included in a container, pack, or dispenser together with instructions for administration.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. The carrier can be a solvent or dispersion medium containing, for example, water, ethanol, a polyol (for example, glycerol, propylene glycol, and liquid polyethylene glycol, and the like), or a suitable mixture thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Typically, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Injectable compositions may contain various carriers such as vegetable oils, dimethylacetamide, dimethylformamide, ethyl lactate, ethyl carbonate, isopropyl myristate, ethanol, and polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil.

Oral compositions typically include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel® (Na Starch Glycolate), or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Alternatively, the pharmaceutical composition can be formulated as a chewing gum, lollipop, or the like.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as known in the art.

In some embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, the compounds provided herein can be formulated or further derivatized to assist the compounds in crossing the blood-brain barrier (BBB). Methods for preparation of such formulations and derivatives will be apparent to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

In all of the methods described herein, appropriate dosages of the compounds can readily be determined by those of ordinary skill in the art of medicine, e.g., by monitoring the patient for signs of disease amelioration or inhibition, and increasing or decreasing the dosage and/or frequency of treatment as desired. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods provided herein, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the compounds described herein, an effective amount (i.e., an effective dosage), ranges from about 0.1 to 100,000 µg/kg body weight. In some embodiments, an effective amount ranges from about 0.1 to 1000 µg/kg body weight, e.g., about 0.1 to 1000 µg/kg body weight, e.g., about 1 to 100 µg/kg body weight, e.g., about 10 to 90 µg/kg body weight, e.g., about 20 to 80 µg/kg body weight, e.g., about 30 to 70 µg/kg body weight, e.g., about 40 to 60 µg/kg body weight, e.g., about 45 µg/kg body weight, e.g., about 50 µg/kg body weight, e.g., about 55 µg/kg body weight. In some embodiments, the dosage is about 25 µmol/kg. Optimal dosage levels can be readily determined by a skilled practitioner, such as a physician, e.g., a neurologist. The compound can be administered one time per day, twice per day, one time per week, twice per week, for between about 1 to 52 weeks per year, e.g., between 2 to 50 weeks, about 6 to 40 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a compound can include a single treatment or, preferably, can include a series of treatments.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of a neurological disorder or one or more symptoms of a neurological disorder. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Methods of Treating or Reducing a Risk of Developing a Neurodegenerative Disease The methods described herein are based in part on the discovery that compounds or pharmaceutical compositions containing a sulfide donor conjugated or unconjugated to an NMDA receptor can be used to inhibit or reduce neuronal death. For example, combining ACS48 and memantine by amide bonding to form S-memantine modified the sulfide-releasing characteristics of ACS48. S-memantine released sulfide at ~2.1 fold higher rate than did ACS48 in cell culture medium. Administration of S-memantine to mice, but not $Na_2S$ or ACS48 alone, increased cerebral sulfide levels. The present disclosure demonstrates that 10 or 50 µM of $Na_2S$ administered pre- or post-oxygen glucose deprivation (OGD) did not improve cell viability of SH-SY5Y subjected to OGD. Similarly, administration of 25 µM of $Na_2S$ 1 minute after reperfusion after bilateral carotid artery occlusion (BCAO) failed to prevent brain injury in mice. In contrast, cell viability of SH-SY5Y cells or primary cortical neurons subjected to OGD were improved by incubation with S-memantine starting at any time between pre-OGD and up to 8 hours after OGD or at 30 minutes or 2 hours after OGD, respectively. Further, these in vitro findings were confirmed by in vivo studies in which administration of S-memantine 1 minute after reperfusion after BCAO markedly improved survival rate and neurological outcomes in mice. Taken together, these results indicate that slow $H_2S$-releasing compounds have higher therapeutic potential against neuronal ischemia than simple sulfide salts. S-memantine markedly improved neurological function and 60-day survival rate and decreased cerebral infarct volume after BCAO. These results validate the neuroprotective effects of $H_2S$-releasing NMDA receptor antagonist in vivo.

Accordingly, in some embodiments of the methods described herein, methods of treating or reducing a risk of developing a neurodegenerative disease, e.g., taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria, are provided. The methods can involve diagnosing a subject, preparing compounds or pharmaceutical compositions comprising a sulfide donor and an NMDA receptor antagonist, administering, e.g., by injection, orally, or via other means of delivery, to a subject, having or at risk for developing a neurodegenerative disease, a therapeutically effective amount of the compound or pharmaceutical composition. The subject can be further monitored for treatment response.

In some embodiments of any of the methods described herein, the subject is suspected of having, is at risk of having, or has a neurodegenerative disease, e.g., taupathies (e.g., Alzheimer's Disease), Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage, e.g., malaria encephalitis or cerebral malaria. It is well within the skills of an ordinary practitioner to recognize a subject that has, or is at risk of developing, a neurodegenerative disease. A subject that has, or is at risk of developing, a neurodegenerative disease is one having one or more symptoms of the condition or one or more risk factors for developing the condition. Symptoms of neurodegenerative diseases are known to those of skill in the art and include, without limitation, tremor, rigidity, slowness of movement, postural instability, disorders of speech, cognition, mood, behavior, and thought, problems with the executive functions of attentiveness, planning, flexibility, and abstract thinking, or impairments in semantic memory, and changes in personality, cognition, and physical skills.

The subjects can also be those undergoing any of a variety of additional anti-neurodegenerative therapy treatments. Thus, for example, subjects can be those being treated with one or more of memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, an acetylcholinesterase inhibitor, tetrabenazine, benzodiazepine, levodopa, a dopamine agonist, a monoamine oxidase-B inhibitor, idebenone, riluzole, interferons, glatiramer acetate, mitoxantrone, and natalizumab.

EXAMPLES

Example 1

Figure 1B:
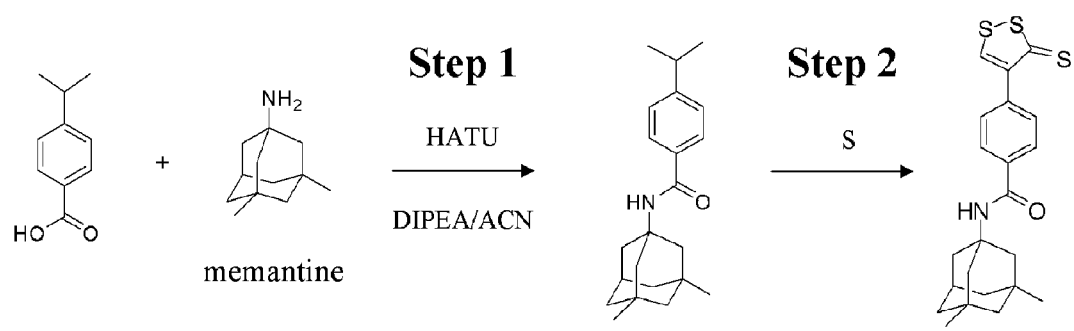
Figure 1C:
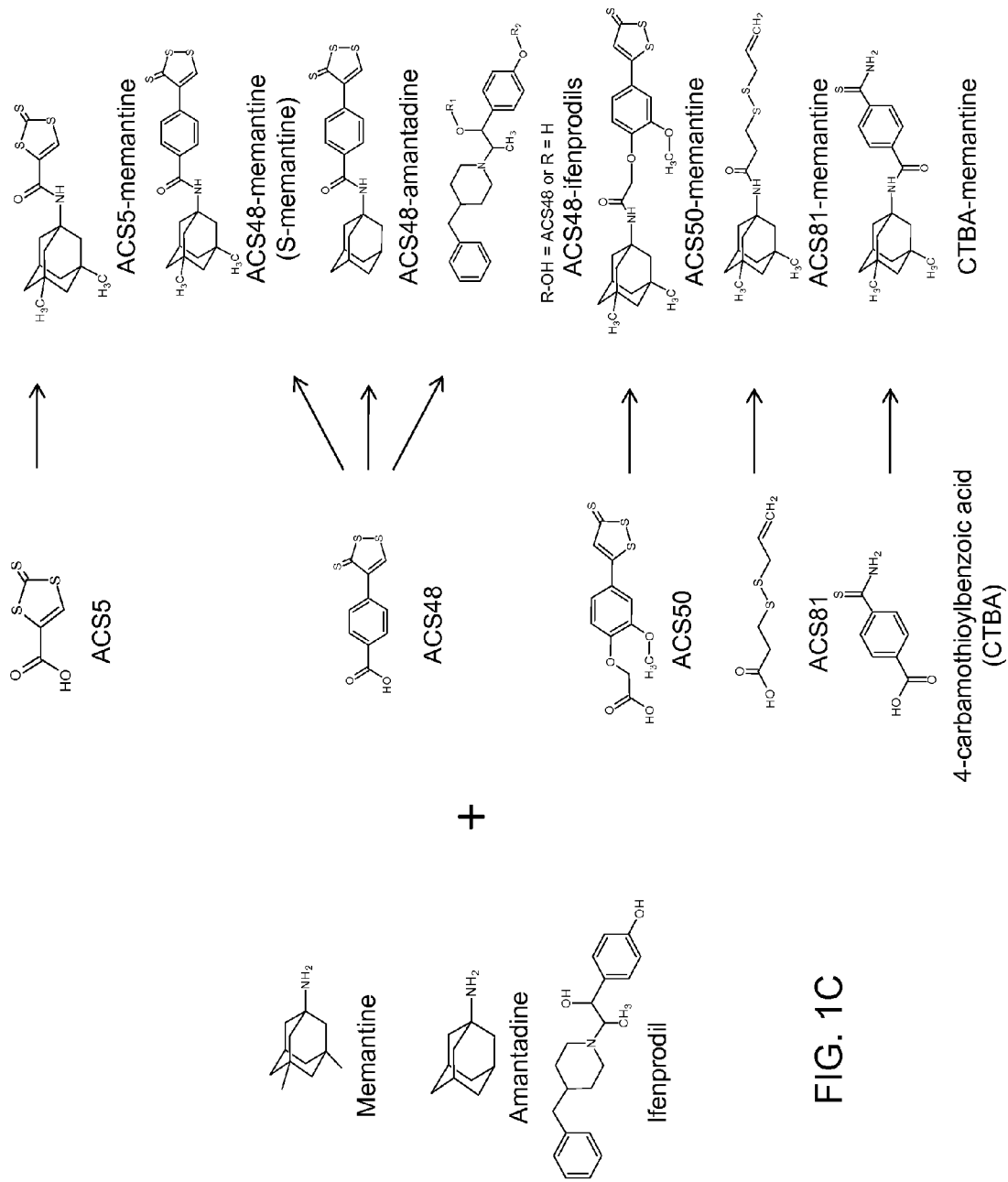

Synthesis of $H_2S$-Releasing NMDA Receptor Antagonist S-Memantine 4-(3-thioxo-3H-1,2-dithiol-4-yl)-benzoic acid (ACS48) was synthesized as described previously (FIG. 1A) (Lee et al. (2010) J Biol Chem 285, 17318-17328). N-((1r,3R,5S,7r)-3,5-dimethyladamantan-1-yl)-4-(3-thioxo-3H-1,2-dithiol-4-yl)-benzamide (i.e., S-memantine) was synthesized using the following two steps as shown in FIG. 1B: First, under nitrogen atmosphere, at room temperature, 4-(propan-2-yl)-benzoic acid (0.5 g; 3.05 mmol) and memantine (0.82 g; 4.57 mmol) were mixed in 5 ml of anhydrous N,N-dimethylformamide (DMF) and N,N,diisopropylethylamine (2.12 ml; 12.19 mmol) was added. After cooling to room temperature, O-(7-azabenzotriazol-1-yl)-N,N,N',N'-tetramethyluronium hexafluorophosphate (HATU) (1.045 g; 2.75 mmol), dissolved in 5 ml of DMF was gradually added, followed by an overnight stirring at room temperature. After evaporation of DMF, extraction and purification, N-((1r,3R,5S,7r)-3,5-dimethyl-adamantan-1-yl)-4-isopropylbenzamide (Amide 1) was obtained. In the second step, under nitrogen atmosphere, sulfur (5.05 g, 158 mmol) was melted at 140° C. and Amide-1 (2.16 g, 13.2 mmol) was added. The reaction mixture was stirred for 24 hours at 190° C. to form a layer of reddish brown solution. After cooling the reaction mixture back to 140° C., 100 ml toluene was added followed by further cooling to room temperature. Acetone was added to form a suspension that was filtered and the filtrate was concentrated to dryness. The dry residue was purified by flash chromatography. Fractions containing pure S-memantine were dried under vacuum to give 0.678 g (19% yield) of reddish brown crystals. The purity of the final product was greater than 98%. The structure of the final product was confirmed by mass spectrometry (Finnigan LCQ Advantage, ESI+) and $^1H$ NMR spectroscopy. C22H25NOS3: m/z calculated: $[M+H]^+$ 415.11. Found: 415.64. $^1H$ NMR (400 MHz, DMSO-d6) 9.21 (s, 1H), 7.82 (d, J=6.8 Hz, 2H), 7.68 (s, 1H), 7.63 (d, J=8.4 Hz, 2H), 2.12-2.14 (m, 1H), 1.92-1.93 (m, 2H), 1.71-1.78 (m, 4H), 1.16-1.39 (m, 6H), 0.86 (s, 6H).

Example 2

Treatment of Cells with $H_2S$ Donor Compounds

Cell Culture—

Human neuroblastoma SH-SY5Y cells were cultured in Eagle's medium/Ham's F-12 50/50 Mix (DMEM/F12, Cellgro by Mediatech, Inc.) supplemented with 10% fetal bovine serum (FBS) and 1% penicillin/streptomycin. The cells were seeded into 96 well plates ($2 \times 10^4$ cells per well) for OGD and measurements of toxicity, 6 cm dishes ($5 \times 10^5$ cells per dish) for measurements of sulfide and reduced-glutathione (GSH), or 10 cm dishes ($1 \times 10^6$ cells per dish) for measurements of intracellular calcium. Cell culture medium was replaced every 2 days, and the cultures were maintained at 37° C. in 95% air/5% $CO_2$ in a humidified incubator. Cells were used after reaching 80% confluent.

Primary neuronal cultures were prepared from the cortex of embryonic day 15 C57BL6J mice. In brief, brains were harvested and the hemispheres were dissected under a microscope. The cortical neurons were dissociated in Neurobasal medium (Gibco) with B27 supplement (antioxidant plus, Gibco). The cells were seeded into 24 well plates coated with poly-D-lysine (Becton Dickinson Labware, $2 \times 10^5$ cells per well), followed by the medium-change with fresh one on the next day. The half of culture medium was replaced with Neurobasal medium witn B27 supplement (antioxidant minus) every other day, and the cultures were maintained at 37° C. in 95% air/5% $CO_2$ in a humidified incubator. Cells were used for experiments 11 days after seeding.

Treatment of Cells with $H_2S$ Donor Compounds—

ACS48 and S-memantine were dissolved in dimethyl sulfoxyde (DMSO), then, diluted to desired concentration with culture medium. The final concentration of DMSO was adjusted to 1%. 1% DMSO did not affect cell viabilities of SH-SY5Y or primary cortical neurons, as confirmed using lactose dehydrogenase (LDH) assay method.

Measurement of Sulfide Levels in SH-SY5Y Cells, Culture Medium, and Murine Plasma and Brain—

Concentration of free sulfide in SH-SY5Y cells was measured using high performance liquid chromatography (HPLC) (Tokuda et al. (2012) Antioxidants & Redox Signaling). Briefly, SH-SY5Y cells were seeded into 6 cm dishes ($5 \times 10^5$ cells per dish). After being 80% confluent, 20 μM $H_2S$ donor was added to the dish and incubated at 37° C. Cells were washed with ice-cold Tris-HCl (100 mM, PH 9.5, DTPA 0.1 mM) buffer, scraped, transferred to microfuge tubes, and centrifuged. MBB (10 mM in acetonitrile, 50 μl) was added to 100 μl of supernatant. After 30 minutes of incubation at room temperature in dark, 50 μl of 200 mM 5-sulfosalicylic acid (SSA) was added. After centrifugation, supernatant was analyzed by HPLC. For sulfide levels in medium, after centrifugation, supernatant was used for MBB reaction as above.

Plasma and brain sulfide levels were measured 90 minutes after intraperitoneal administration of $Na_2S$, ACS48, or S-memantine. Blood was drawn from left ventricle and centrifuged to collect the plasma. After perfusion with Tris-HCl buffer via left ventricle, brain was harvested, homogenized in Tris-HCl, and centrifuged. Plasma and supernatant of brain homogenate were derivatized with MBB and analyzed by HPLC.

Figure 2A:
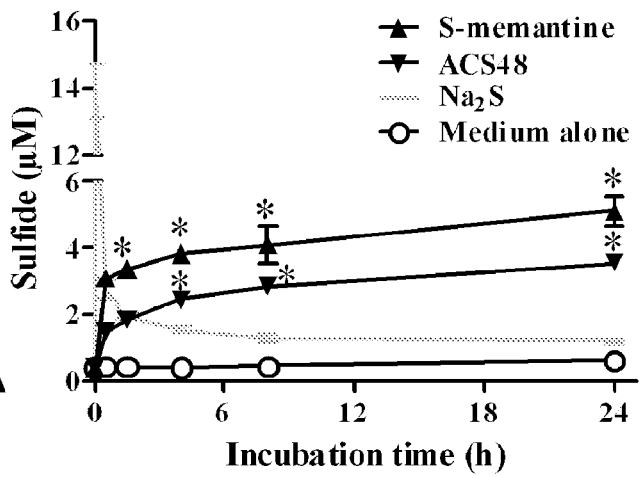
FIGS. 2A-C are a series of line graphs showing (A) Sulfide levels (µM) released from 20 µM $Na_2S$ (no symbol), ACS48 (▼), S-memantine (▲), and medium alone (●) in DMEM/F12 supplemented with 10% FBS. Mediums were incubated at 37° C. for 0 minutes, 1 minute (only $Na_2S$), 30 minutes, 1.5 hours, 4 hours, 8 hours, or 26 hours after addition of $H_2S$ donor. N=3 each. Values of the medium alone group differ significantly from all other groups at all time points except for $Na_2S$ at 8 hours and 26 hours ($P<0.05$), ACS48 differs significantly from S-memantine at all time points ($P<0.01$), * $P<0.01$ vs. $Na_2S$ by two-way ANOVA with Bonferroni post-test; (B) Intracellular sulfide levels of SH-SY5Y treated with 20 µM $Na_2S$ (no symbol), ACS48 (▼), S-memantine (▲), and medium alone (●) in DMEM/F12 with 1% DMSO. Cells were incubated at 37° C. for 0 minutes, 30 minutes, 1.5 hours, 4 hours, 8 hours, or 26 hours after addition of $H_2S$ donor. N=3 each. * $P<0.001$ vs. all other groups by two-way ANOVA with Bonferroni post-test; and (C) Intracellular sulfide levels of SH-SY5Y treated with S-memantine (line with no symbol, 20 µM), ACS48 (■, 20 µM), ACS48+memantine (□, 20 µM+20 µM), memantine (○, 20 µM), and medium alone (●) in DMEM/F12 with 1% DMSO. Cells were incubated at 37° C. for 0 minutes, 30 minutes, 1.5 hours, 4 hours, or 8 hours after addition of $H_2S$ donor. N=3 each. No significant was found difference between "with memantine" and "without memantine."

To determine the timing and levels of sulfide release by different sulfide donors, sulfide concentrations after addition of $Na_2S$, ACS48, or S-memantine to the Dulbecco's modification of DMEM/F12 with 10% FBS (without cells) was measured using HPLC as reported (Tokuda et al. (2012) Antioxidants & Redox Signaling). FIG. 2A shows time-dependent changes of sulfide concentrations in the medium after addition of 20 µM of each compound at time 0 at pH 7.4. Although $Na_2S$ raised sulfide levels immediately, sulfide levels induced by $Na_2S$ decreased rapidly and became lower than sulfide levels induced by ACS48 and S-memantine at 1.5 hours and 8 hours after addition to the medium, respectively (P<0.01 by two-way ANOVA with Bonferroni post-test). ACS48 and S-memantine increased sulfide levels to 3.6 µM and 5.1 µM after 24 hours, respectively. Sulfide levels in the medium were higher after addition of S-memantine than ACS48 at all time points examined (~2.1 fold, P<0.01 by two-way ANOVA with Bonferroni post-test). Interestingly, both ACS48 and S-memantine released very little sulfide in PBS whereas ACS48 released more sulfide than did S-memantine in Tris-HCl (pH 9.5) and in DMEM/F12 without FBS.

Figure 2B:
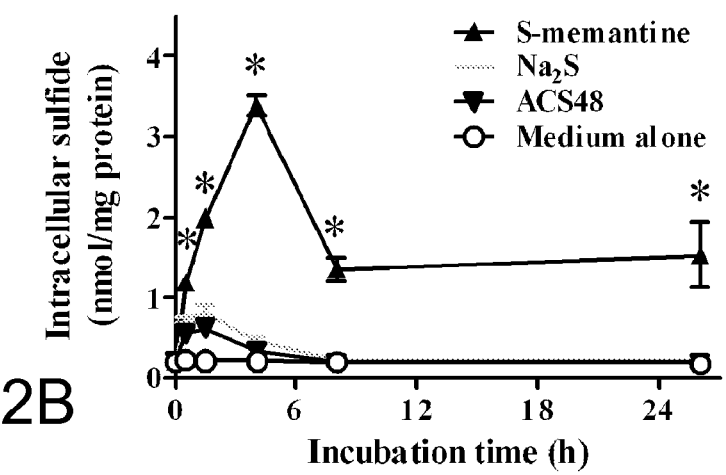
Figure 2C:
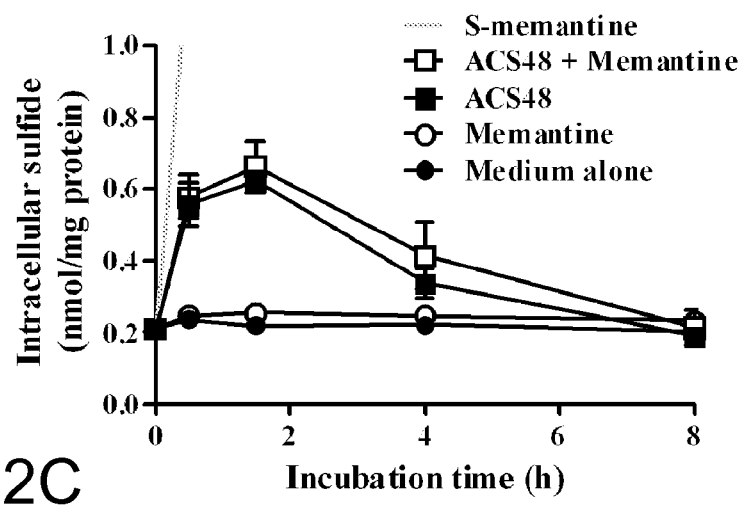

Incubation of SH-SY5Y cells with $Na_2S$, ACS48 and S-memantine increased intracellular sulfide levels with different magnitude and time course. Intracellular sulfide levels peaked around 1.5 hours after addition of $Na_2S$ and ACS48 to the medium that disappeared by 8 hours (FIG. 2 B). In contrast, incubation of SH-SY5Y cells with S-memantine increased intracellular sulfide level more markedly than incubation with ACS48 at all time points after addition (~10 fold at 4 hours, P<0.001 by two-way ANOVA with Bonferroni post-test). In a separate experiment, we examined whether or not incubation with memantine itself or incubation with ACS48 and memantine would affect intracellular sulfide levels in SH-SY5Y cells. Memantine itself did not affect intracellular sulfide levels in SH-SY5Y cells incubated with or without ACS48 (FIG. 2C). Hence, chemical bonding between ACS48 and memantine is important for the high intracellular sulfide levels achieved after addition of S-memantine.

Example 3

Oxygen-Glucose Deprivation (OGD)

Figure 3A:
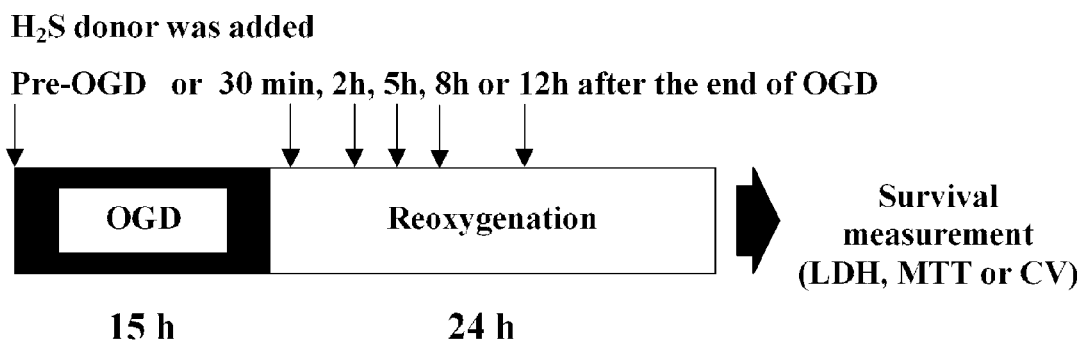
FIGS. 3A-B are schematic diagrams of protocols of Oxygen-Glucose Deprivation (OGD) for SH-SY5Y cells and murine primary cortical neurons, respectively.

OGD for SH-SY5Y was performed by placing cells in a hypoxia chamber (STEMCELL Technologies Inc.) for 15 hours, followed by 24 hours of reoxygenation as previously reported (FIG. 3A) (Serra-Pérez et al. (2008) Journal of Neurochemistry 106, 1237-1247). Briefly, medium was replaced with glucose-free RPMI 1640 with L-glutamine (Cellgro by Mediatech, Inc), deoxygenated with anaerobic gas mixture (93% $N_2$-5% $CO_2$-2% $H_2$) for 30 minutes before use. Cells were then placed in a hypoxia chamber, flushed with anaerobic gas mixture (93% $N_2$-5% $CO_2$-2% $H_2$) and incubated at 37° C. After 15 hours of hypoxia, medium was replaced with DMEM/F12 and incubated for 24 hours at 37° C. in 95% air/5% $CO_2$ in a humidified incubator.

Figure 3B:
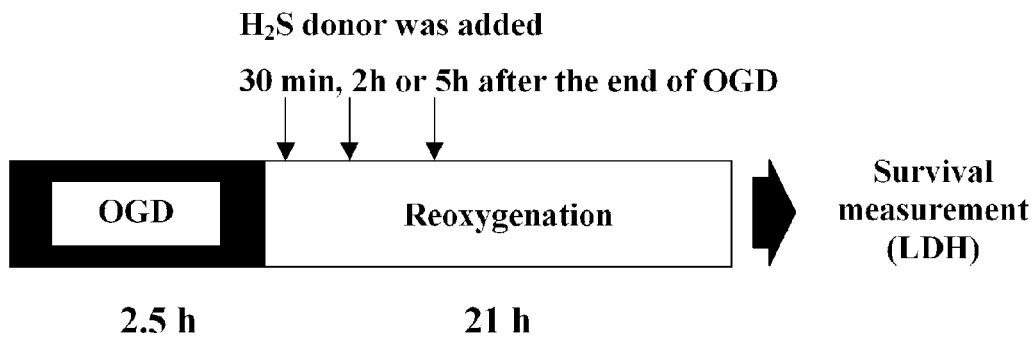

OGD for primary cortical neurons was performed with the similar protocol as above (FIG. 3B). Briefly, the culture medium was replaced with deoxygenated Neurobasal medium without glucose, and then placed in the hypoxic chamber for 2.5 hours. After OGD, the medium was replaced with Neurobasal medium with glucose and incubated for 21 hours at 37° C. in 95% air/5% $CO_2$ in a humidified incubator. Control cells without OGD and reoxygenation were incubated in the fresh Neurobasal medium with glucose and incubated for 21 hours at 37° C. in 95% air/5% $CO_2$, then, used for viability experiment.

Figure 4:
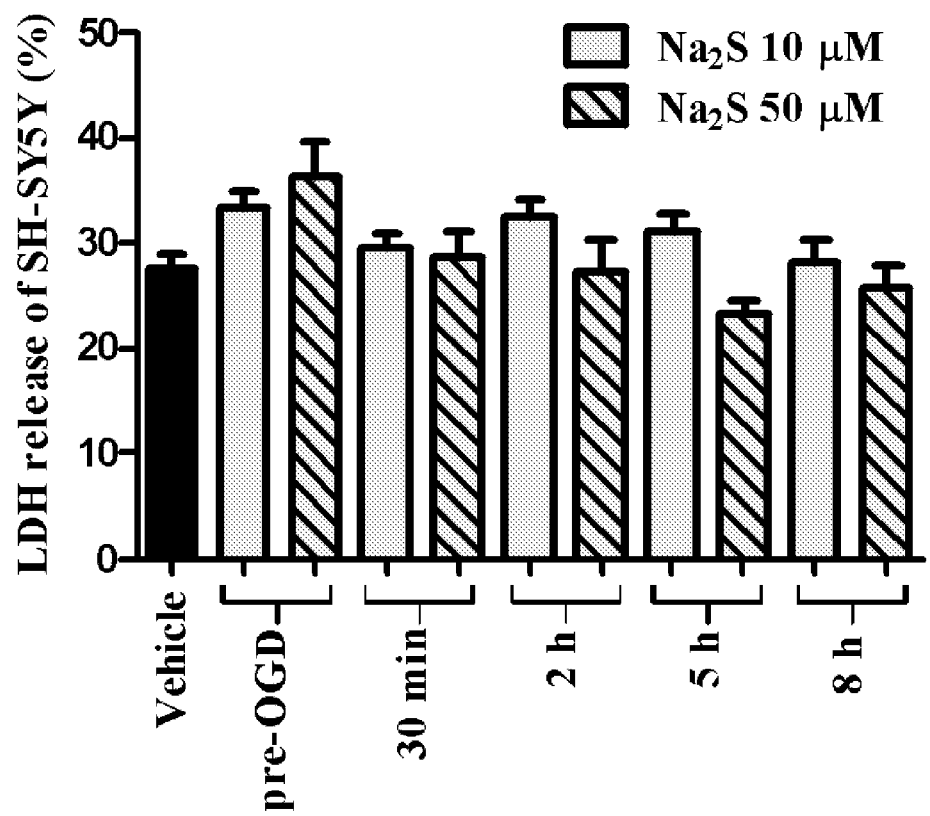
FIG. 4 is a bar graph showing the effects of $Na_2S$ on LDH-release from SH-SY5Y after OGD. $Na_2S$ at 10 or 50 µM, or vehicle was added at pre-OGD or 30 minutes, 2 hours, 5 hours, or 8 hours after the end of OGD. LDH released in the culture medium was measured 24 hours after the end of OGD. N=5-8 each. No significant difference was found between vehicle and $Na_2S$.

The effect of $Na_2S$ was examined since it has been widely used as a therapeutic compound against neuronal ischemia in vitro. Fifteen hours of OGD followed by 24 hours of reoxygenation induced cell death in SH-SY5Y cells as indicated by increased LDH release into the medium. Addition of $Na_2S$ to the culture medium at various time points (pre-OGD or 0.5, 2, 5, and 8 hours after the end of OGD) and concentrations (10 and 50 µM) failed to improve cell viability (FIG. 4).

Figure 5A:
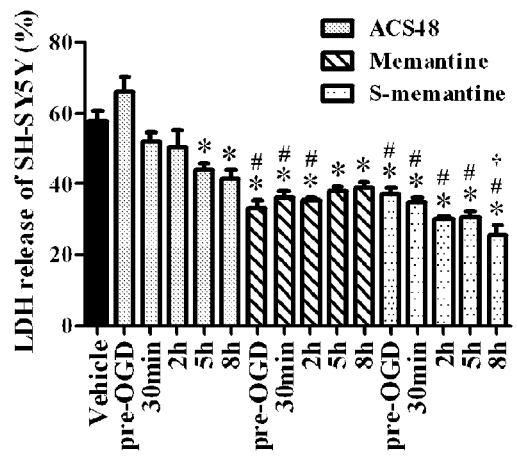
FIGS. 5A-D is a series of four bar graphs depicting (A and B) Time dependence of the effects of $H_2S$ donors on LDH-release from SH-SY5Y (or murine primary cortical neurons) after OGD. ACS48, memantine, S-memantine at 10 µM or vehicle was added at 5 minutes before the initiation of OGD (pre-OGD) or 30 minutes, 2 hours, 5 hours, or 8 hours (or 30 minutes, 2 hours, or 5 hours for primary neurons) after the end of OGD. LDH released in the culture medium was measured 24 hours (or 21 hours for primary neurons) after the end of OGD. N=5 or 6 each. * $P<0.001$ vs. vehicle, # $P<0.01$ vs. ACS48 added at same time point. † $P<0.05$ vs. memantine added at same time point; and (C and D) Dose dependence of the effects of $H_2S$ donors on LDH-release from SH-SY5Y (or murine primary cortical neurons) after OGD. ACS48, memantine, S-memantine at 10 or 50 µM or vehicle was added 8 hours (or 30 minutes for primary neurons) after the end of OGD. LDH released in the culture medium was measured 24 hours (or 21 hours for primary neurons) after the end of OGD. N=5 or 6 each. * $P<0.01$ vs. vehicle, # $P<0.05$ vs. ACS48 at same dose. † $P<0.01$ vs. memantine at same dose.
Figure 5B:
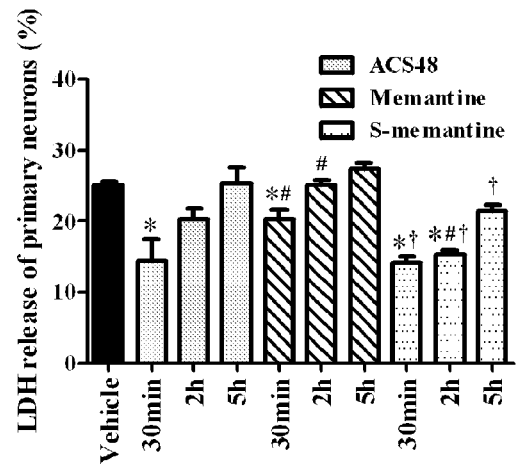
Figure 5C:
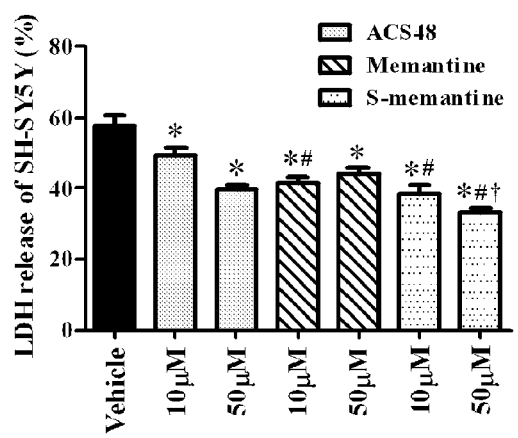
Figure 5D:
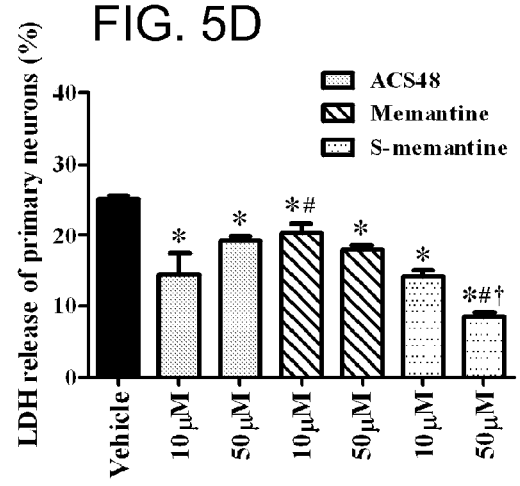

The ability of ACS48, memantine, and S-memantine to improve viability of SH-SY5Y cells subjected to 15 hours of OGD followed by 24 hours of reoxygenation was examined. Based on time- and dose-range studies, it was determined that 50 µM was the most effective dose and at 8 hours after the end of OGD was the most effective time point to add ACS48 or S-memantine to improve viability of SH-SY5Y cells after OGD (FIGS. 5A and B). Addition of S-memantine to the medium at 50 µM at 8 hours after the end of OGD improved the viability of SH-SY5Y cells more markedly than did addition of ACS48 or memantine at the same dose and time point, as indicated in LDH release, MTT, and CV assays (FIGS. 6A, B, C, and D).

Example 4

LDH Assay

A microtiter plate containing cells was centrifuged at 250×g for 10 minutes and the supernatant was used for LDH measurement with LDH Cytotoxicity Detection Kit (Roche). After aspirating the medium, remaining cells were washed with PBS, then, 100 µl of 1% Triton-X was added to each well, followed by incubation at 37° C. for 30 minutes. Medium and lysates were used for LDH measurement at wavelength 492 nm. Percentage of released LDH was calculated with following formula: {LDH (medium)/LDH (medium+cell)×100}. Average value of control (cells without OGD) was deducted as background.

This assay was used to access ability of ACS48, memantine, and S-memantine to improve survival of murine primary cortical neurons after 2.5 hours of OGD followed by 21 hours of reoxygenation. Based on dose- and time-range studies (FIGS. 5A and B), ACS48 and S-memantine was added at 50 µM at 30 minutes after the end of OGD. S-memantine exhibited more robust neuroprotective effects compared to ACS48 or memantine (FIG. 6E).

Figure 7:
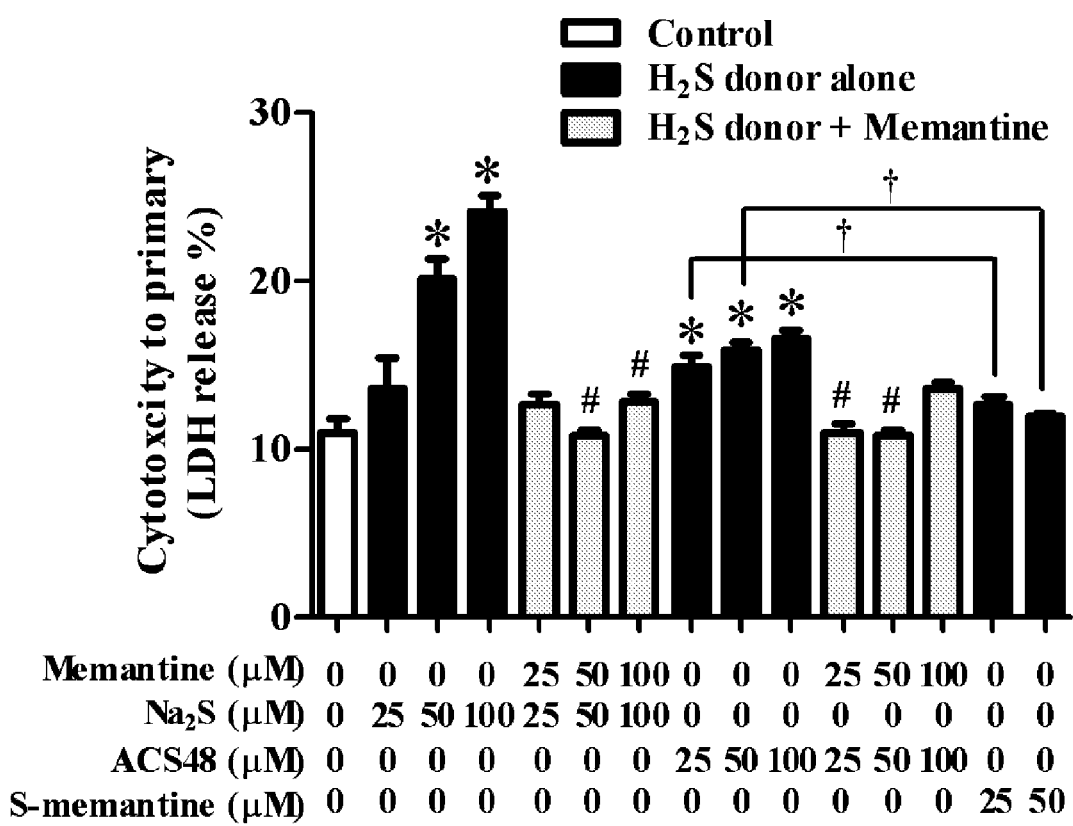
FIG. 7 is a bar graph depicting cytotoxicity of $Na_2S$, ACS48, and S-memantine. LDH in the culture medium released from murine primary cortical neurons were measured 24 hours after treatment with $Na_2S$, ACS48, or S-memantine at 25, 50, or 100 µM with or without 0, 25, 50, or 100 µM memantine. N=5 or 6 each. * $P<0.001$ vs. vehicle without memantine, # $P<0.001$ vs. same dose of the same $H_2S$ donor without memantine, † $P<0.05$.

To define the role of NMDA receptor in cytotoxicity of $H_2S$, we examined whether or not memantine suppresses toxicity of $Na_2S$ and ACS48 to murine primary cortical neurons. LDH released from primary cortical neuron was measured 24 hours after addition of $Na_2S$ or ACS48 with or without memantine (FIG. 7). Although incubation with $Na_2S$ or ACS48 at 50 µM markedly increased LDH release in the murine primary cortical neurons, LDH release caused by $Na_2S$ or ACS48 was abolished by co-incubation with 50 µM of memantine, suggesting the critical role of NMDA receptor activation in the cytotoxicity of $H_2S$. Although S-memantine increased intracellular sulfide levels more robustly than $Na_2S$ and ACS48, incubation with S-memantine at 50 µM did not induce LDH release from primary cortical neurons. These observations demonstrate that S-memantine retains the ability to antagonize NMDA receptor.

Example 5

3-(4,5-dimethylthiazol-2-yl)-2,5-diphenyltetrazolium bromide (MTT) assay

Ten µl of thiazolyl blue tetrazolium bromide solution (5 mg/ml in PH 7.4 PBS) was added to each well containing 100 µl of medium and cells, followed by incubation at 37° C. for 4 hours in the dark. Isopropanol (100 µl, 0.04 N HCl) was added to dissolve blue dye. After dissolved completely, absorbance was measured with plate-reader (Synergy 2, BioTek Instrument) at test wavelength 570 nm and reference wavelength 670 nm. Cell viability was determined by absorbance at 570 nm and reported as ratio to control cells (without OGD).

Example 6

Crystal Violet (CV) Assay

After aspirating culture medium, cells were fixed and stained by 0.5% CV in 95% (v/v) ethanol for 5 minutes, then washed by tap water several times. After taking photographs, 1% sodium dodecylsulfate solution was added to each well to elute blue dye. Absorbance was measured with plate-reader at 595 nm of wavelength. Values were shown as ratio to control (cells without OGD).

Example 7

Measurement of Intracellular Calcium Level in Murine Primary Cortical Neurons Intracellular calcium level was measured by a previously-described method using Fura-2/AM with some modifications (Gao et al. (2008) European Journal of Pharmacology 591, 73-79). Briefly, cells were trypsinized, pelleted, resuspended in the medium, and incubated with 5 µM Fura-2/AM (Invitrogen) in HEPES buffer (pH 7.4, NaCl 110 mM, KCl 2.6 mM, $MgSO_4$ 1 mM, $CaCl_2$ [Fisher Scientific], 1 mM, HEPES 25 mM, and glucose 11 mM) at 37° C. for 40 minutes, and then washed twice. Cells were resuspended in HEPES buffer and transferred to a cuvette. $Na_2S$, ACS48, memantine, or S-memantine at 20 µM was added to the cuvette with or without glutamate (100 µM), respectively. Final cell concentration was 1×10$^5$ cells/ml. The fluorescence intensity ratio was measured with Spectra Max M5 (Molecular Devices, CA, USA) at wavelength of $\lambda_{ex}$=340/380 nm and $\lambda_{em}$=510 nm.

Figure 8A:
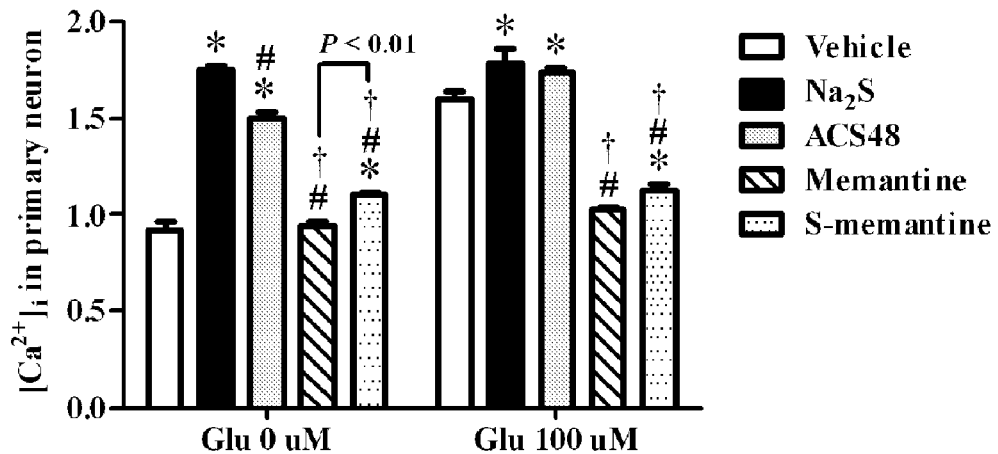
FIGS. 8A-B is a series of two bar graphs showing intracellular calcium levels $[Ca^{2+}]i$ in (A) murine primary cortical neurons incubated with 20 µM of $Na_2S$, ACS48, memantine, or S-memantine with or without 0.1, 2, or 5 mM of Glutamate (Glu). Values are shown as fura-2 fluorescence intensity ratio ($\lambda_{ex}$ 340 nm/$\lambda_{ex}$ 380 nm). N=5 each. * P<0.001 vs. vehicle with the same dose of Glu, # P<0.01 vs. Na$_2$S with the same dose of Glu. † P<0.05 vs. ACS48 with the same dose of Glu; and (B) Intracellular GSH levels [GSH]i of SH-SY5Y was measured 8 hours after incubation with 50 µM ACS48, memantine, or S-memantine with or without 2 mM of glutamate. Values were normalized with protein concentration in lysate and reported as a ratio to the values of vehicle-treated group without Glu. N=4 each. * P<0.05 vs. vehicle w/o Glu, # P<0.01 vs. vehicle with Glu, † P<0.05 vs. ACS48 and memantine without Glu, ‡ P<0.01 vs. Na$_2$S, ACS48, and memantine with Glu.
Figure 8B:
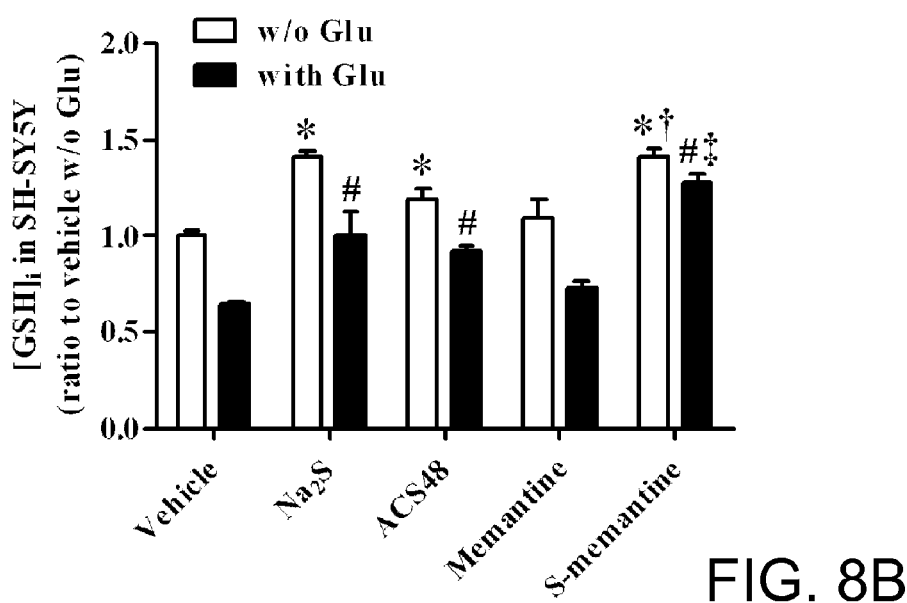

Activation of NMDA receptor increases intracellular calcium concentration (Nakamura et al. (2010) Cell Calcium 47, 190-197; Yong et al. (2010) Neurochemistry International 56, 508-515). The influence of 20 µM $Na_2S$, ACS48, S-memantine, and memantine on intracellular calcium levels ($[Ca^{2+}]_i$) was examined in murine primary cortical neurons incubated with or without glutamate using previously reported approach with some modifications (Micu et al. (2006) Nature 439, 988-992). Incubation with $Na_2S$ or ACS48, but not memantine or S-memantine, without glutamate increased $[Ca^{2+}]_i$ in SH-SY5Y primary cortical neurons (FIG. 8A). While incubation with $Na_2S$, ACS48, or S-memantine without glutamate increased $[Ca^{2+}]_i$ in murne primary cortical neurons, magnitude of calcium accumulation induced by S-memantine was markedly smaller than that induced by $Na_2S$ or ACS48. Similarly, S-memantine or memantine suppressed calcium accumulation in primary cortical neurons induced by 100 µM glutamate, whereas $Na_2S$ or ACS48 augmented glutamate-induced calcium accumulation.

Example 8

Measurement of Intracellular GSH Levels in SH-SY5Y

Intracellular GSH level of SH-SY5Y was measured using HPLC method as previously reported (Kimura et al. (2009) Antioxidants & Redox Signaling 12, 1-13). Briefly, cells were seeded into 6 cm dishes (5×10$^5$ cells per dish) and treated with 50 µM $H_2S$ donors or memantine with or without 2 mM glutamate for 8 hours, followed by washing with ice-cold PBS. Cells were scraped and transferred to a microfuge tube and sonicated. Some fraction of lysate was used for protein assay. After centrifugation, 75 µl of supernatant, 26 µl of 2-(cyclohexylamino) ethanesulfonic acid (CHES, 0.5 M, PH 8.4), and 4 µl of 50 µM MBB were mixed and incubated at room temperature in dark for 30 minutes. Acetic acid (100 µl, 30% v/v) was added, followed by centrifugation at 15,000×g for 10 min after 5 min incubation of the tube on ice. The supernatant was analyzed using HPLC at wavelength of $\lambda_{ex}$=370 nm and $\lambda_{em}$=486 nm.

Without glutamate, incubation with 50 µM of $Na_2S$, ACS48, or S-memantine increased intracellular GSH levels in SH-SY5Y cells. While glutamate decreased GSH levels in cells incubated with medium alone (P<0.001 by two-way ANOVA with Bonferroni post-test), incubation with $Na_2S$, ACS48, or S-memantine restored intracellular GSH levels. Further, the magnitude of increase of GSH levels after incubation with S-memantine was greater than with $Na_2S$ or ACS48 (FIG. 8C). Memantine per se did not affect GSH levels.

Example 9

Measurement of Protein Levels and Phosphorylation

Protein levels in SH-SY5Y were determined by standard immunoblot techniques using primary antibodies (1:1,000, Cell Signaling Technology Inc., Danvers, Mass.) against cleaved caspase-3, caspase-3, phosphorylated Akt at threonine 308, Akt, phosphorylated $ERK_{1/2}$ at threonine 202 and tyrosine 204, $Erk_{1/2}$, β-tubulin and phosphorylated tau protein at serine 202 and threonine 205 (1:250; Thermo scientific, MN1020), tau protein (1:1000; Thermo scientific, MN1010). Bound antibody was detected with a horseradish peroxidase-linked antibody directed against rabbit IgG (1:10,000~1:25,000; Cell Signaling Technology Inc.), or mouse IgG (1:2,000; GE healthcare, NA931V) and was visualized using chemiluminescence with ECL Advance kit (GE healthcare).

S-memantine, but not memantine, at 50 µM added 8 hours after the end of OGD prevented caspase-3 activation in SH-SY5Y subjected to 15 hours of OGD followed by 24 hours of reoxygenation. S-memantine or memantine did not affect Akt phosphorylation. S-memantine, but not memantine, attenuated dephosphorylation of ERK (FIG. 9).

Example 10

Global Cerebral Ischemia and Reperfusion Experiments in Mice

After approval by the Massachusetts General Hospital Subcommittee on Research Animal Care, all animal experiments were performed in accordance with the guidelines of the National Institutes of Health. Male mice (C57BL/6J, 8-9 weeks old) were purchased from the Jackson Laboratory (Bar Harbor, Me.) and given access to food and water ad libitum in our animal facility until the time of experiments. Mice were anesthetized with ketamine (80 mg/kg, i.p.) and xylazine (12 mg/kg, i.p.). Body temperature was kept at 37±0.5° C. during whole procedure. Cerebral ischemia was induced by 40 minutes of bilateral common carotid artery occlusion (BCAO) with microsurgical clips. $Na_2S$, ACS48, S-memantine, or memantine at 25 µmol/kg or vehicle was intraperitoneally administered 1 minute after the initiation of reperfusion. After reperfusion and recovery from anesthesia, mice were intraperitoneally given 1 ml of 5% dextrose-enriched lactated Ringer's solution daily for 1 week. Neurological score was evaluated as described previously (Thal et al. (2010) Journal of Neuroscience Methods 192, 219-227). Next, eight items were checked and scored to evaluate neurological scores. 1. Grasping movement reflex (inducing the catching reflex by running a little rod over the plantar surface of the paw): 0-4 points; 2. Stop at the edge of a table: 0 or 1 point; 3. Turning the head (turning the head when touching the ear from behind with a little rod): 0-2 points; 4. Falling reflex (lifting the mouse at the tail and lowering with the front legs towards the ground): 0 or 1 point; 5. Spontaneous motility (moving behavior on a flat surface): 0-2 points; 6. Circling behavior (moving behavior on a flat surface): 0 or 2 points; 7. Pelt property (appearance of the coat): 0 or 1 point; and 8. Flight reaction (spontaneous behavior on a flat surface): 0 or 1 point. Total of 14 points. Higher score means worse neurological function.

Treatment of Mice with $H_2S$ Donor Compounds—

ACS48 and S-memantine were dissolved in the corn oil/DMSO (v/v, 95/5) suspension. $Na_2S$ was dissolved in saline 5 minutes before administration. Mice were intraperitoneally given 4 μl/g of these solutions 1 minute after reperfusion following 40 minutes of BCAO.

Figure 10A:
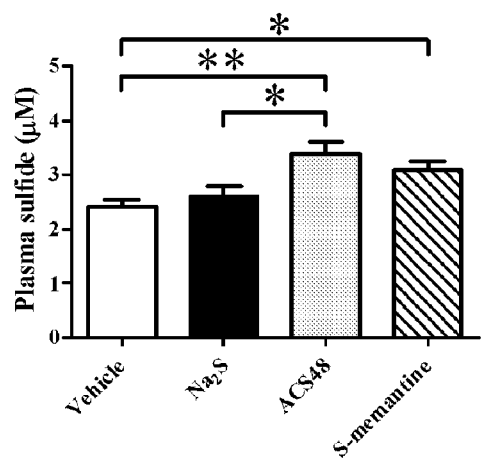
FIGS. 10A-B is a panel of two bar graphs showing (A) plasma and (B) cerebral sulfide levels of mice, measured 90 minutes after intraperitoneal administration of Na$_2$S, ACS48, or S-memantine at 25 µmol/kg. N=4 each. * P<0.05, ** P<0.01.
Figure 10B:
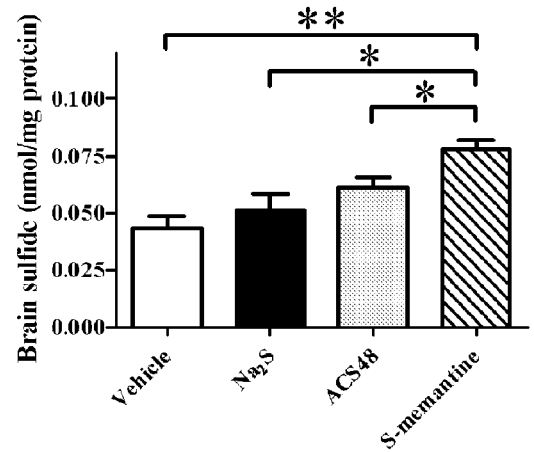

To define the impact of S-memantine on systemic sulfide concentrations, plasma and cerebral sulfide levels were measured 90 minutes after intraperitoneal administration of $Na_2S$, ACS48, or S-memantine at 25 μmol/kg in mice using HPLC (FIGS. 10A and B). ACS48 and S-memantine, but not $Na_2S$, increased plasma sulfide levels. Cerebral sulfide levels were increased after treatment with S-memantine, but not after $Na_2S$ or ACS48.

Measurement of Cerebral Infarct Volume after BCAO—

Mice were decapitated and brains were harvested 24 hours after BCAO and reperfusion. Coronal sections (2 mm thickness) of the cerebrum were then soaked into 1% 2,3,5-triphenyltetrazolium chloride (TTC) solution in PBS at 37° C. for 30 minutes. After taking photographs under the same condition, infarct volume was calculated with image J software ver. 1.44. Photographs were gray-scaled, then, brighter area than threshold determined using Image J software was calculated as infarct area. Values were shown as ratio of cerebral infarct volume to total volume. The average value of the brighter region volume in control mice was deducted from calculated area as background.

Pretreatment of Drug and Lippopolysaccharide (LPS)-Induced Cognitive Impairment—

C57BL6J mice (9-10 weeks old, male) were intraperitoneally administered vehicle (saline), $Na_2S$ (90 μmol/kg), S-memantine (90 μmol/kg), or memantine (45 or 90 μmol/kg) 30 min before LPS-challenge. *E. coli* LPS (Sigma-aldrich, lot 070M4018) at 250 μg/kg was intraperitoneally administered once a day for 7 days.

Morris Water-Maze—

The water maze consisted of a painted circular pool (200 cm diameter and 30 cm high) in which mice were trained to escape from the water by swimming to a hidden platform (15 cm diameter, 1.5 cm beneath the water's surface). Water was kept at 20° C. and opacified with titanium dioxide for all training and testing. The experiments were recorded using a camera connected to a video recorder and a computerized tracking system. Mice were trained twice a day on days 1-3 and given drug pretreatment followed by LPS-challenge on day 4-10. Test trials were carried out 4 hours after LPS-challenge on days 4-6.

Measurement of Amyloid Beta Concentration in Mice Cortex and Hippocampus—

Mice which underwent LPS-challenge for 7 days were sacrificed and their brains were harvested after perfusion with PBS. Cortex and hippocampus were separated and kept at −80° C. before using. $A\beta_{42}$ concentrations were measured by ELISA kit (Invitrogen) in accordance with manufacturer's instructions.

Data Analysis—

All data are presented as means±SE. Data were analyzed by ANOVA using Sigmastat 3.01a (Systat Software Inc., Chicago, Ill.) and Prism 5 software package (GraphPad Software, La Jolla, Calif.). Newman-Keuls multiple comparison post hoc test or Bonferroni post hoc test were respectively performed for One-way Anova or Two-way Anova test as required. P values less than 0.05 were considered significant.

S-Memantine Attenuated Brain Damage and Improved Survival and Neurological Function after Global Cerebral Ischemia and Reperfusion in Mice.

Figure 11A:
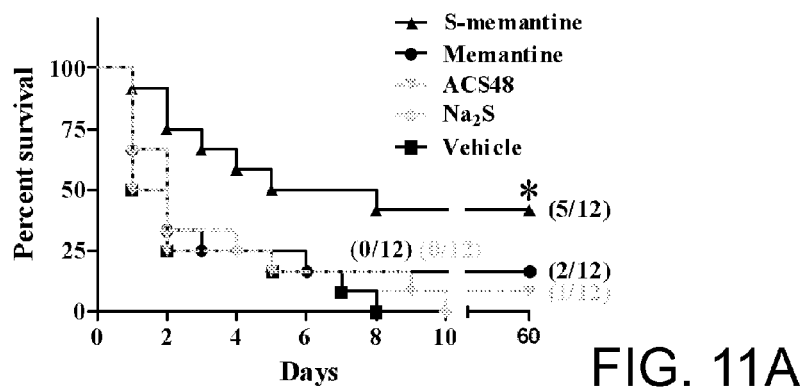
FIGS. 11A-C is a series of graphs and photographs showing (A) Percent survival of mice subjected to 40 minutes of bilateral carotid artery occlusion (BCAO) and reperfusion and treated with S-memantine, memantine, ACS48, Na$_2$S, or vehicle 1 minute after reperfusion. N=12 each. * P<0.05 vs. Na$_2$S, ACS48, memantine, and vehicle by log-rank test; (B) Neurological score after BCAO. Vehicle and ACS48 (N=12, 6, 3, 3, 3 on day 0, 1, 2, 3, 4, respectively), Na$_2$S (N=12, 8, 4, 4, 4), memantine (N=12, 8, 3, 3, 3), S-memantine (N=12, 11, 8, 7, 7), Sham (N=5). *, , or * P<0.05, 0.01, or 0.001 vs. vehicle; and (C) Cerebral infarct volume and representative photographs of TTC-stained brain of mice subjected to sham operation or BCAO and treated with vehicle or S-memantine. N=5 each. *** P<0.001 vs. vehicle by unpaired t-test.
Figure 11B:
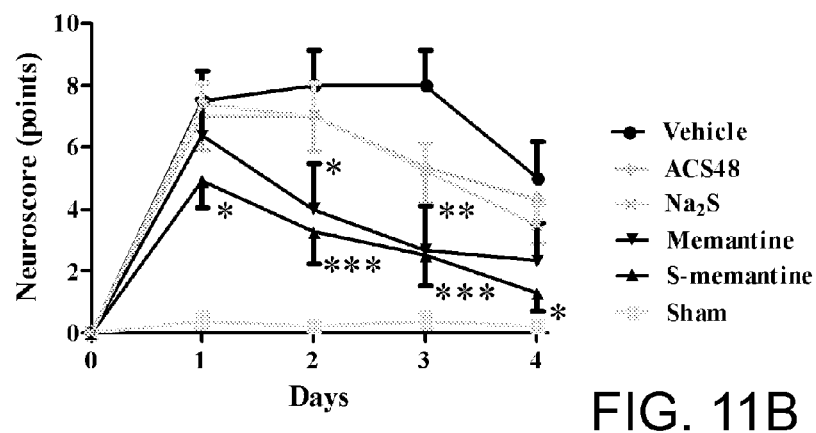
Figure 11C:
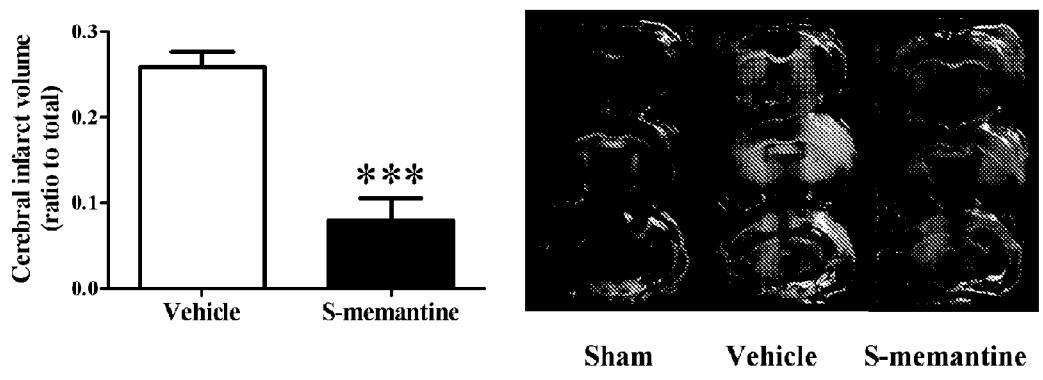

To validate the neuroprotective effects of S-memantine in vivo cerebral ischemia, the ability of $Na_2S$, ACS48, S-memantine, or memantine at 25 μmol/kg to attenuate cerebral injury after BCAO in mice was examined. Vehicle (corn oil/DMSO suspension) did not affect survival of mice after BCAO and reperfusion. $Na_2S$, ACS, or S-memantine at 25 μmol/kg did not affect body temperature. All vehicle- or $Na_2S$-treated mice died in 8 or 10 days (75% or 67% died in 2 days), respectively, whereas treatment with ACS48, memantine, or S-memantine enabled 1, 2, or 5 mice to survive for more than 60 days, respectively. S-memantine-treated mice exhibited markedly higher survival rate than vehicle, $Na_2S$, ACS48, or memantine-treated mice ($P<0.05$ by log-rank test). There was no significant difference in survival rate among $Na_2S$, ACS48, memantine, and vehicle groups (FIG. 11A). S-memantine and memantine improved neurological score on day 1-4 and day 2-3 after BCAO, respectively ($P<0.05$ by two-way ANOVA with Bonferroni test, FIG. 11B). S-memantine markedly decreased cerebral infarct volume compared to vehicle (FIG. 11C, $P<0.001$ vs. vehicle by unpaired t-test).

S-Memantine Attenuated Amyloid Beta-Induced Neuronal Toxicity.

Figure 13A:
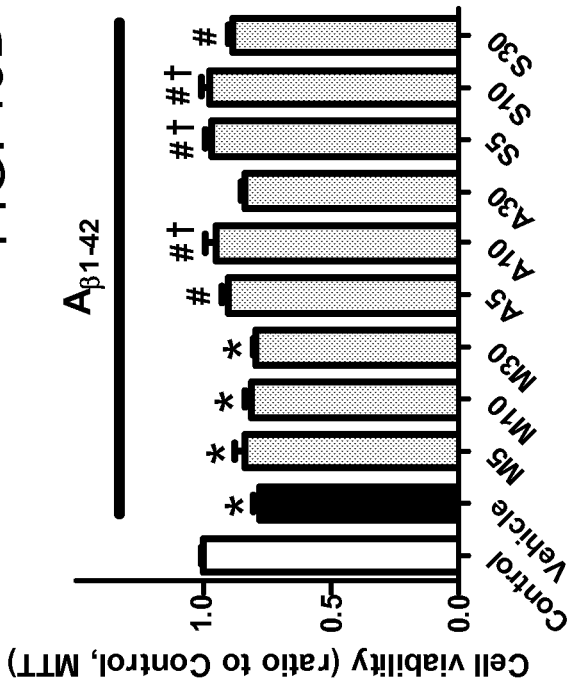
FIG. 13A-B is a set of two bar graphs depicting cell viability of murine primary cortical neurons exposed to 20 µM amyloid beta (Aβ) and treated with memantine, ACS48, or S-memantine at 5, 10, or 30 µM. Cell viability was estimated by LDH release assay in the left graph and MTT assay in the right graph.
Figure 13B:
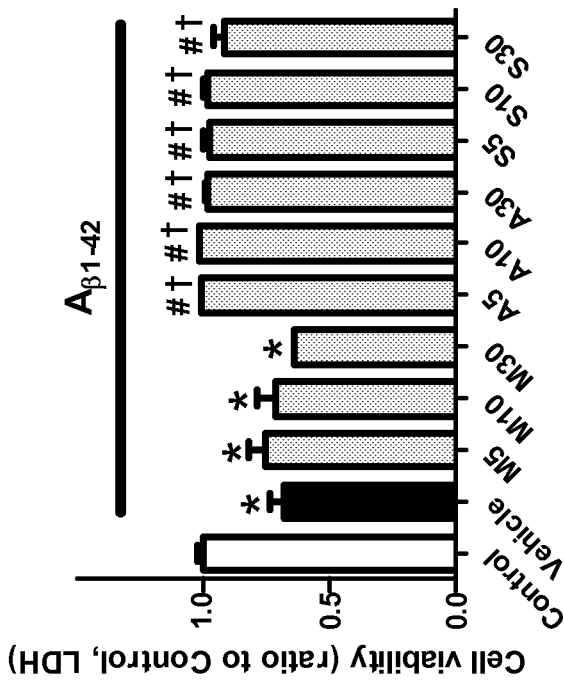
Figure 14:
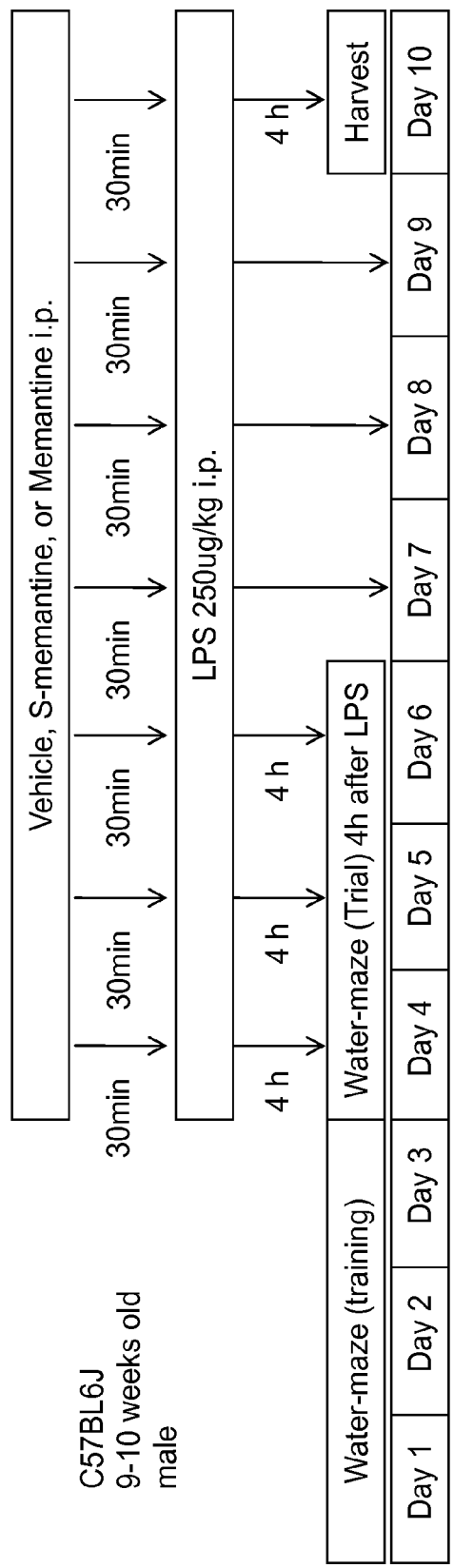
FIG. 14 is a schematic diagram of the protocol of LPS-induced cognitive impairment.

S-memantine, memantine, and ACS48 improved cell viabilities of SH-SY5Y (FIG. 12) and murine primary cortical neurons (FIG. 13) 24 hours after incubation with $A\beta_{1-42}$ at 20 μM. S-memantine and ACS48 improved cell viabilities more markedly than did memantine.

S-Memantine Attenuated Cognitive Impairment Induced by LPS Challenge.

Pretreatment with S-memantine or $Na_2S$ at 90 μmol/kg, but not memantine at 45 or 90 μmol/kg, improved latency until getting platform in Morris water-maze test 4 hours after LPS-challenge (FIG. 15). Memantine at 90 μmol/kg slowed swimming speed, while vehicle, S-memantine, and $Na_2S$ at 90 μmol/kg or memantine at 45 μmol/kg did not change it.

S-Memantine Prevented Amyloid Beta Accumulation in Cortex and Hippocampus.

Figure 16A:
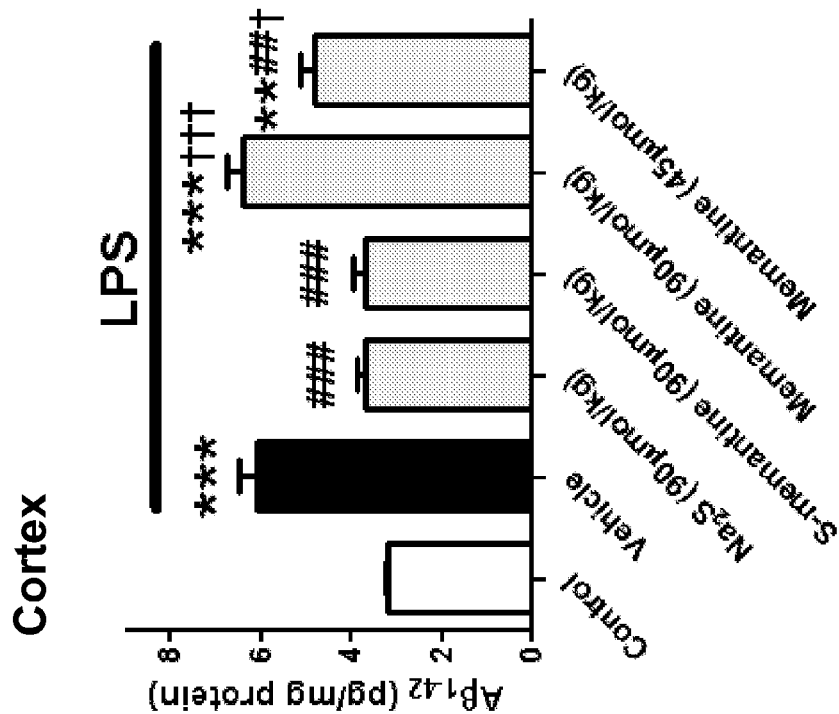
FIG. 16A-B is a panel of two bar graphs showing amyloid beta accumulation after LPS challenge for 7 days in the brain regions of mice.
Figure 16B:
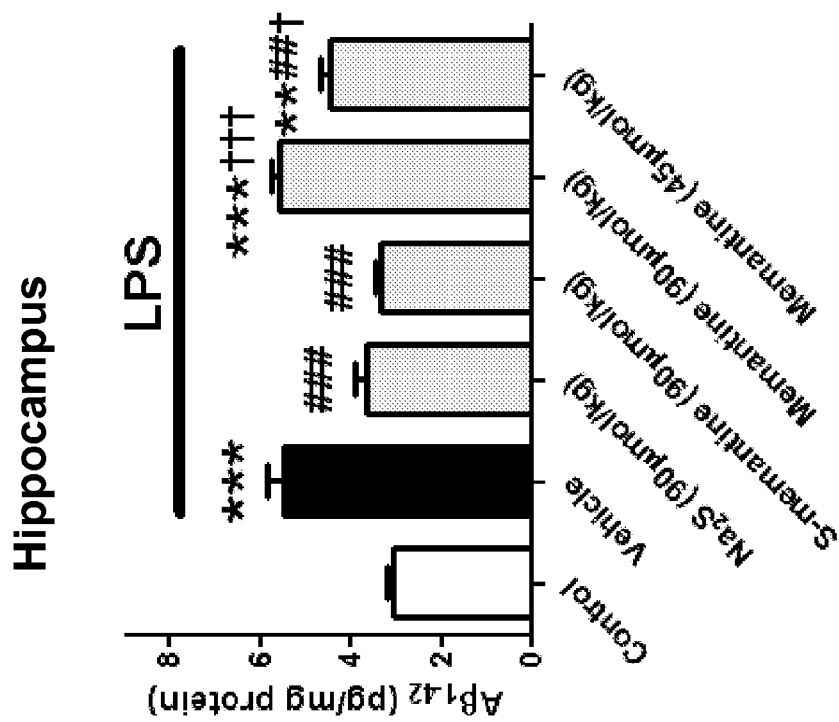

Pretreatment with S-memantine or $Na_2S$ at 90 μmol/kg or memantine at 45 μmol/kg, but not memantine at 90 μmol/kg, prevented $A\beta_{1-42}$ accumulation in mice cortex, or hippocampus (FIG. 16). S-memantine and $Na_2S$ prevented $A\beta_{1-42}$ accumulation more markedly than did memantine.

S-Memantine Prevented Tau Phosphorylation.

Figure 17:
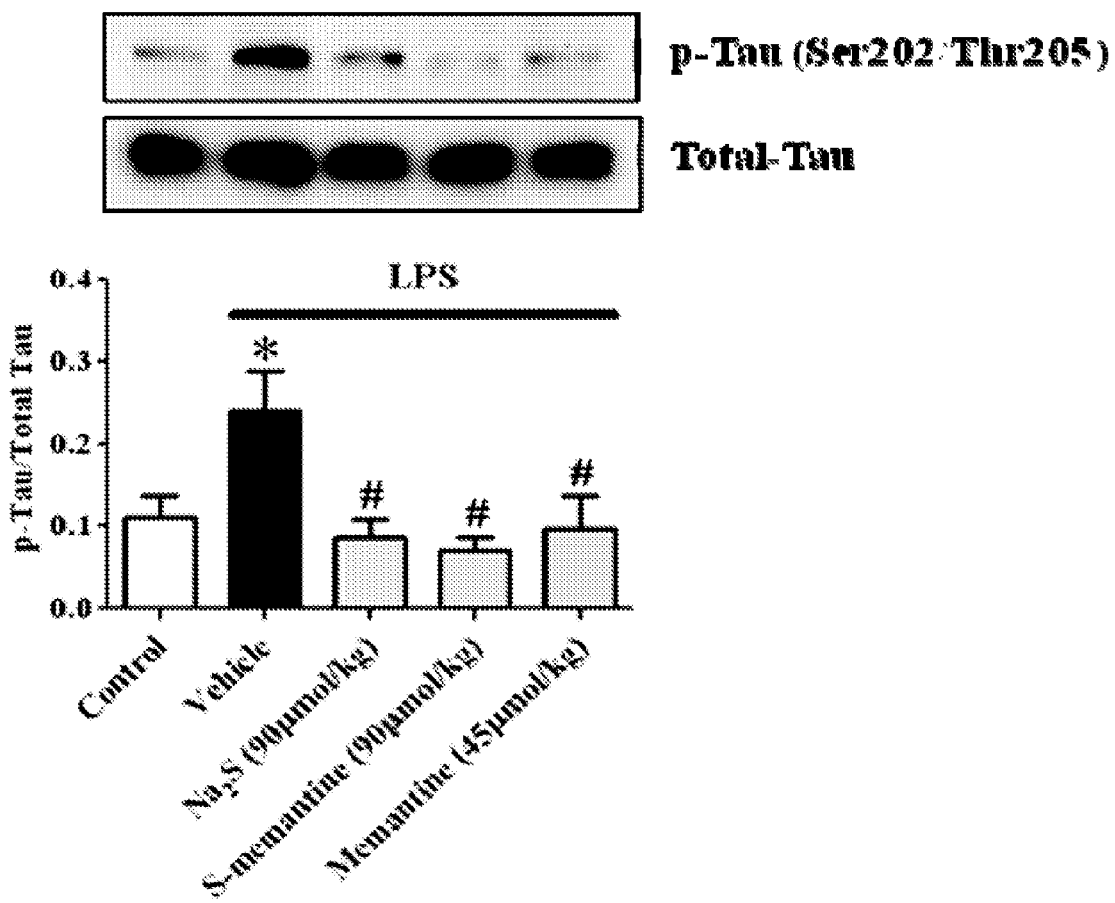
FIG. 17 is a series of photomicrographs and a bar graph depicting representative immunoblot and densitometric analysis of phosphorylated tau protein and tau protein in mice challenged with LPS.

Pretreatment with S-memantine or $Na_2S$ at 90 μmol/kg or memantine at 45 μmol/kg prevented LPS-induced tau phosphorylation at serine 202 and threonine 205 in mice hippocampus (FIG. 17).

Example 11

Treatment of H2S-Releasing NMDA Receptor Antagonists and 1-Methyl-4-Phenylpyridinium (MPP+)-Induced Cytotoxicity The abilities of ACS48-amantadine, CTBA-memantine, S-memantine, and ACS81-memantine to improve viabilities of SH-SY5Y cells incubated with MPP+, which has been used for an in-vitro Parkinson's disease model (Robert et al. (2012) *Cell Death and Differentiation*, 19, 1769-1778), were examined. SH-SY5Y cells (96 well plate, 2×10$^5$ cells/well) were incubated with MPP+ (Sigma-Aldrich) at 5 mM in DMEM/F12 at 37° C. for 24 h. ACS48-amantadine, CTBA-memantine, S-memantine, or ACS81-memantine was dissolved in DMSO and added at 5 or 20 μM to the medium 30 min after the addition of MPP+. The final concentration of DMSO in the medium was adjusted to 0.5% (v/v). Cell viabilities of SH-SY5Y 24 h after the addition of MPP+ were measured by CV assay or MTT assay.

Figure 18A:
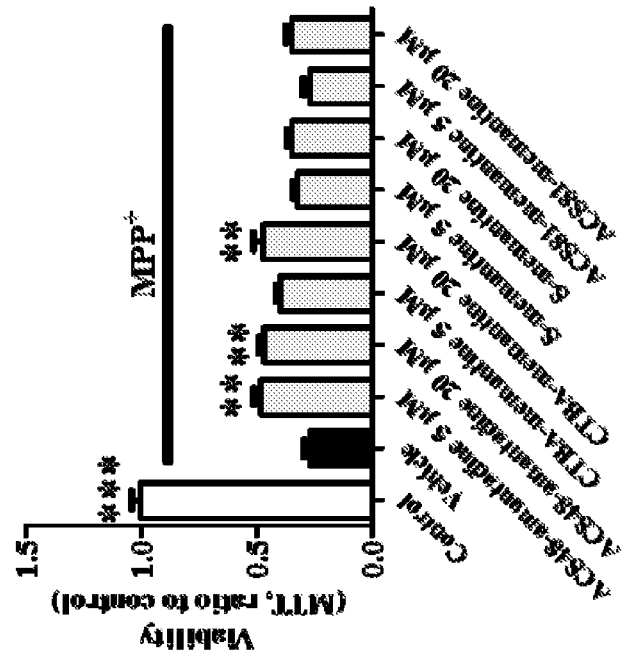
FIG. 18A-B is a set of two bar graphs showing cell viability of SH-SY5Y cells exposed to 5 mM 1-methyl-4-phenylpyridinium (MPP$^+$) for 24 h. ACS48-amantadine, CTBA-memantine, S-memantine, or ACS81-memantine was added at 5 or 20 µM to the medium 30 min after the addition of MPP$^+$. Cell viability was estimated by CV assay in the left graph and MTT assay in the right graph.
Figure 18B:
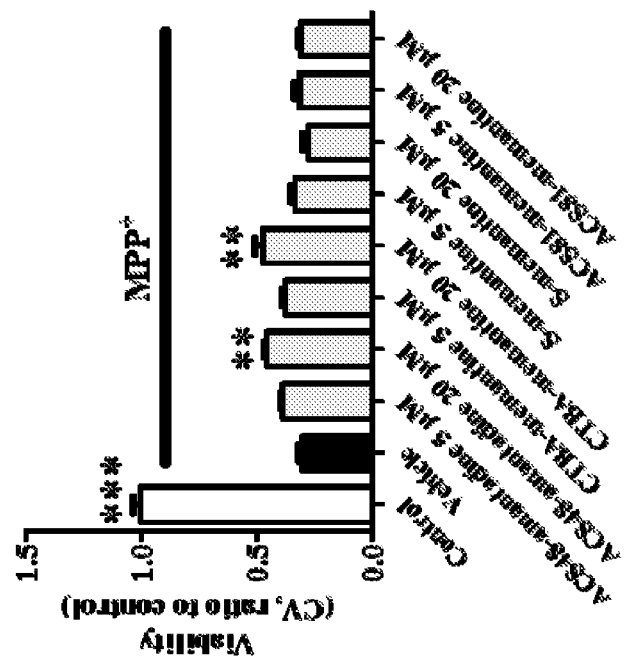

ACS48-amantadine (5 and or 20 μM) and CTBA-memantine (20 μM) added 30 min after the addition of MPP+ improved cell viabilities of SH-SY5Y cells (FIG. 18).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising a sulfide donor conjugated to an N-methyl-D-aspartate (NMDA) receptor antagonist.

2. The compound of claim 1, wherein the compound has a structure of Formula (I):

R$^1$—X$^1$—R$^2$—X$^2$—R$^3$ or a pharmaceutically acceptable salt thereof,
wherein:
R$^1$ is an NMDA receptor antagonist;
X$^1$ is absent or selected from the group consisting of: —NH—, —CO—, —COO—, —OCO—, —NHCO—, —CONH—, —S—, —S—S—, —S—S—S—, (C$_1$-C$_{20}$)alkylene; and a (C$_1$-C$_{20}$)alkylenehalide;
R$^2$ is absent or is selected from the group consisting of: —NH—, —CO—, —COO—, —OCO—, —NHCO—, —CONH—, —S—, —S—S—, —S—S—S—, (C$_1$-C$_{20}$)alkylene; and a (C$_1$-C$_{20}$)alkylenehalide;
X$^2$ is absent or selected from the group consisting of: —NH—, —CO—, —COO—, —OCO—, —NHCO—, —CONH—, —S—, —S—S—, —S—S—S—, (C$_1$-C$_{20}$)alkylene; and a (C$_1$-C$_{20}$)alkylenehalide; and
R$^3$ is a sulfide donor.

3. The compound of claim 1, wherein the sulfide donor comprises a moiety selected from the group consisting of: S—S—S; S—S;

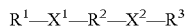

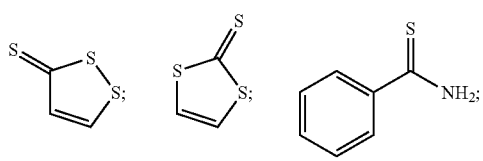

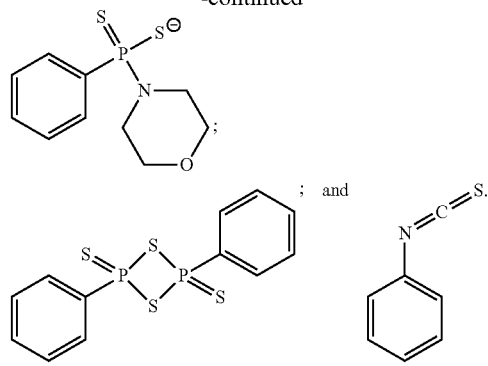

4. The compound of claim 1, wherein the sulfide donor is selected from the group consisting of ACS48, ACS5, ACS50, ACS81, 4-carbamothioylbenzoic acid, Na$_2$S, NaHS, potassium sulfide, potassium hydrosulfide, magnesium sulfide, calcium sulfide, sulfide salt hydrate, p-(methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione.

5. The compound of claim 1, wherein the NMDA receptor antagonist is selected from the group consisting of memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof.

6. The compound of claim 1, wherein the sulfide donor is ACS48 and the NMDA receptor antagonist is memantine.

7. The compound of claim 1, wherein the sulfide donor and the NMDA receptor antagonist are conjugated by an amide linkage, a sulfonamide linkage, a phosphoramide linkage, an ester linkage, an ether linkage, a thioether linkage, or an amine linkage.

8. The compound of claim 1, wherein the compound is N-((1r;3R,5S,7r)-3,5-dimethyladamantan-1-yl)-4-(3-thioxo-3H-1,2-dithiol-4-yl)-benzamide (S-memantine).

9. The compound of claim 2, wherein R$^1$ is selected from the group consisting of:

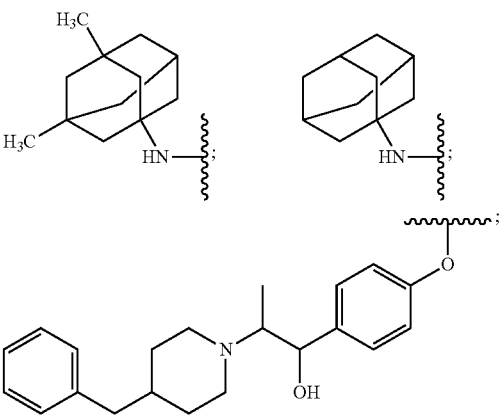

-continued
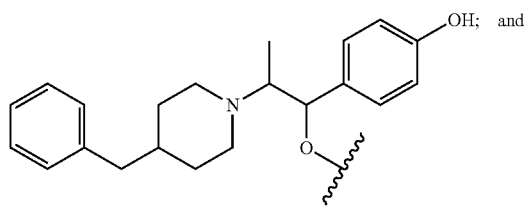
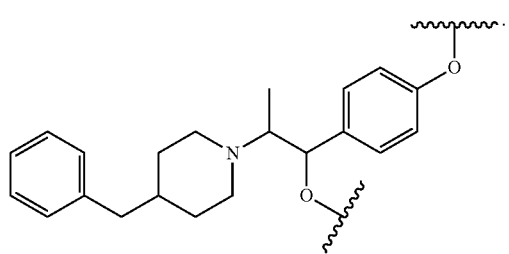
10. The compound of claim 2, wherein $X^1$ is absent.
11. The compound of claim 2, wherein $X^2$ is absent.
12. The compound of claim 2, wherein $R^3$ is selected from the group consisting of:
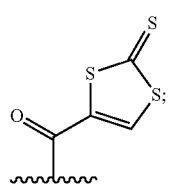 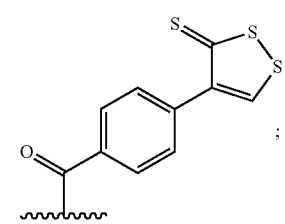
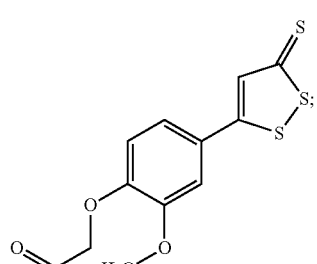
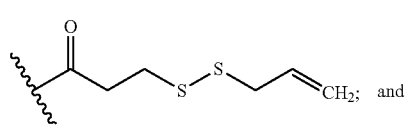
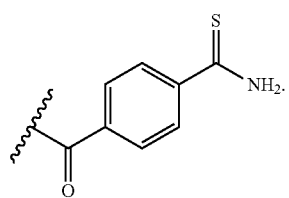
13. The compound of claim 1, wherein the compound is selected from the group consisting of:
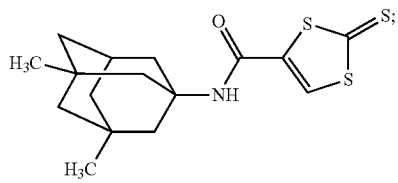
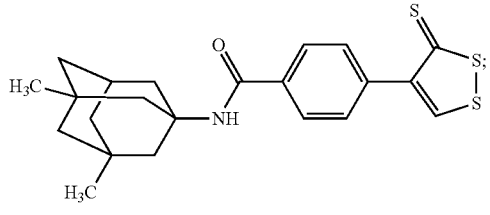
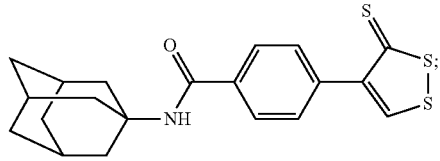
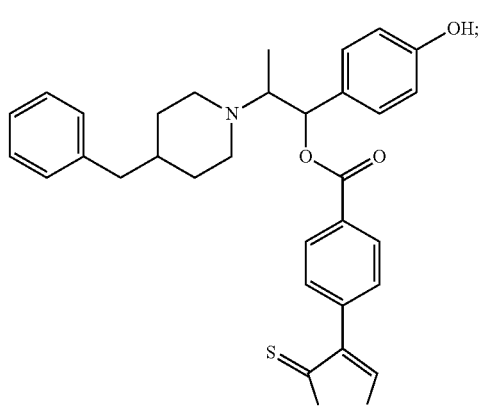
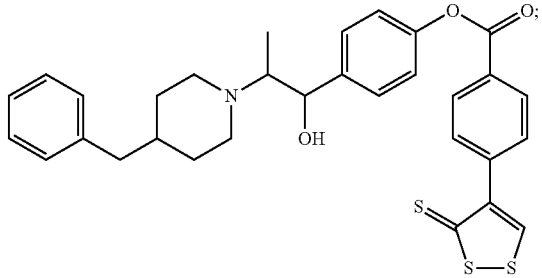
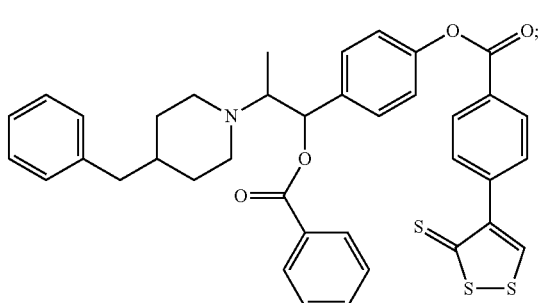

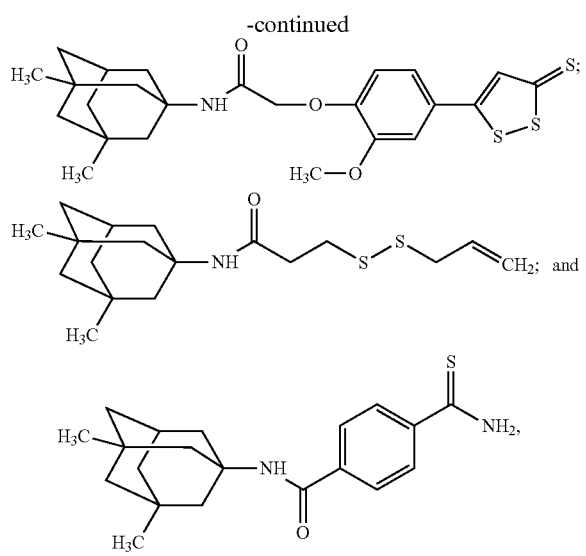

or a pharmaceutically acceptable salt thereof.

14. A pharmaceutical composition comprising a compound of claim 1, or a pharmaceutically acceptable salt thereof; and a pharmaceutically acceptable carrier.

15. A pharmaceutical composition comprising a sulfide donor, an NMDA receptor antagonist, and a pharmaceutically acceptable carrier.

16. The pharmaceutical composition of claim 15, wherein the sulfide donor is selected from the group consisting of ACS48, ACS5, ACS50, ACS81, 4-carbamothioylbenzoic acid, $Na_2S$, NaHS, potassium sulfide, potassium hydrosulfide, magnesium sulfide, calcium sulfide, sulfide salt hydrate, p-methoxyphenyl)morpholino-phosphinodithioic acid, Lawesson's reagent, L-cysteine, S-allyl-L-cysteine, S-propargil-L-cysteine, diallyl disulfide, diallyl trisulfide, allycin, and 5-(4-hydroxyphenyl)-3H-1,2-dithiole-3-thione.

17. The pharmaceutical composition of claim 15, wherein the NMDA receptor antagonist is selected from the group consisting of memantine, amantadine, ifenprodil, ketamine, nitro-memantine, R-2-amino-5-phosphonopentanoate, 2-amino-7-phosphonoheptanoic acid, 3-[(R)-2-carboxypiperazin-4-yl]-prop-2-enyl-1-phosphonic acid, delucemine, dextrallorphan, dextromethorphan, gacyclidine, methoxetamine, neramexane, phencyclidine, remacemide, tiletamine, and pharmaceutically acceptable salts thereof.

18. A method of treating or reducing a risk of developing a neurodegenerative disease in a subject, the method comprising administering to a subject a therapeutically effective amount any one of claim 1, thereby treating or reducing the risk of developing a neurodegenerative disease in the subject.

19. The method of claim 18, wherein the neurodegenerative disease is selected from the group consisting of Alzheimer's Disease, Huntington's Disease, Parkinson's Disease, Friedreich's ataxia, amyotrophic lateral sclerosis, multiple sclerosis, ischemic brain injury, and glaucoma, and encephalitis-, meningitis-, and trauma-induced inflammatory neuronal damage.

20. The method of claim 18, the method further comprising administering to the subject an anti-neurodegenerative therapy.

* * * * *